(12) United States Patent
Hanna et al.

(10) Patent No.: US 6,576,262 B1
(45) Date of Patent: Jun. 10, 2003

(54) METHODS AND APPARATUS FOR PARTICLE FORMATION

(75) Inventors: Mazen Hermiz Hanna, Heaton (GB); Peter York, Ilkley (GB)

(73) Assignee: Nektar Therapeutics, San Carlos, CA (US)

( * ) Notice: Subject to any disclaimer, the term of this patent is extended or adjusted under 35 U.S.C. 154(b) by 0 days.

(21) Appl. No.: 09/700,441

(22) PCT Filed: Apr. 29, 1999

(86) PCT No.: PCT/GB99/01337

§ 371 (c)(1), (2), (4) Date: Mar. 8, 2001

(87) PCT Pub. No.: WO99/59710

PCT Pub. Date: Nov. 25, 1999

(30) Foreign Application Priority Data

May 15, 1998 (GB) .............................................. 9810559

(51) Int. Cl.[7] .............................. A61K 9/14; A61K 9/16
(52) U.S. Cl. ........................ 424/489; 424/489; 424/490
(58) Field of Search .................................. 424/489, 490

(56) References Cited

FOREIGN PATENT DOCUMENTS

| WO | WO 96/00610 | 1/1996 |
| WO | WO 97/31691 | 9/1997 |
| WO | WO 98/36825 | 8/1998 |

*Primary Examiner*—Thurman K. Page
*Assistant Examiner*—Amy E Pulliam
(74) *Attorney, Agent, or Firm*—Michael J. Rafa; Felissa H. Cagan

(57) ABSTRACT

The invention provides a method for forming particles of a target substance (26), involving: (a) preparing a solution or suspension of the substance in a vehicle (21) which is or includes either a near-critical fluid (21) or a first supercritical fluid; (b) introducing the solution or suspension into a particle formation vessel (32); and (c) contacting the solution or suspension, in the particle formation vessel, with a second super-critical fluid, under conditions which allow the second supercritical fluid to cause precipitation of particles of the target substance from the solution or suspension; wherein the second supercritical fluid is miscible or substantially miscible with the vehicle and is a fluid in which the target substance is insoluble or substantially insoluble. Also provided is apparatus for use in carrying out an embodiment of the method, including a particle formation vessel and means for controlling the temperature and pressure inside it; a fluid mixing vessel and means for controlling the temperature and pressure inside it; first fluid inlet means for introducing into the fluid mixing vessel a vehicle and a solution of a target substance in a primary solvent, so as to form in the fluid mixing vessel a solution of the substance and the primary solvent in the vehicle; and second fluid inlet means for introducing the solution thus formed, preferably together with a second supercritical fluid, into the particle formation vessel. The invention also provides a particulate product formed using the method.

15 Claims, 16 Drawing Sheets

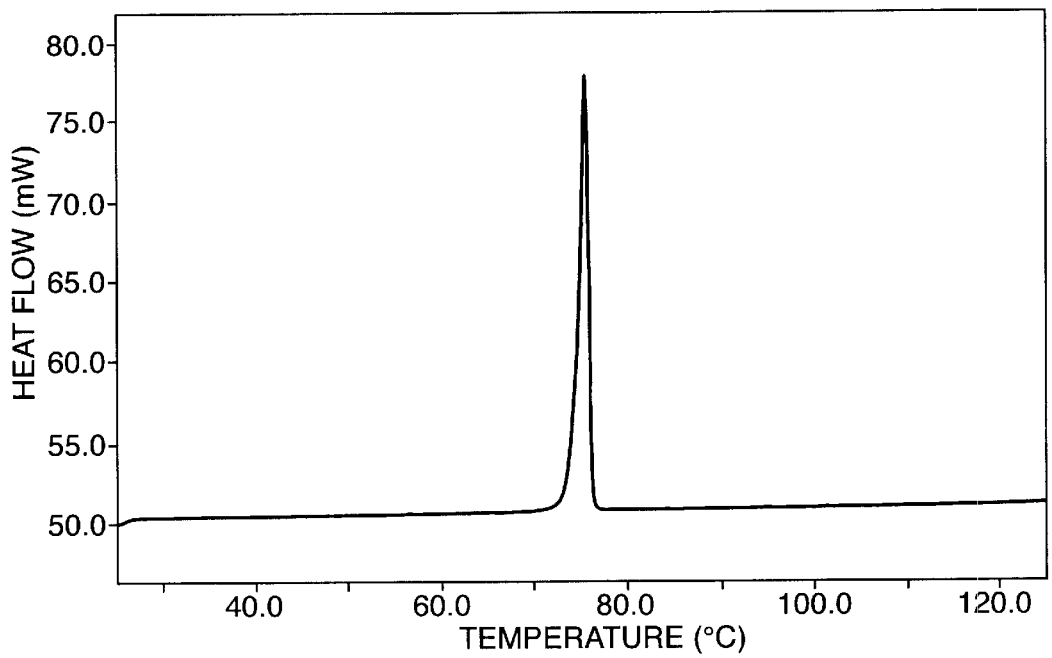
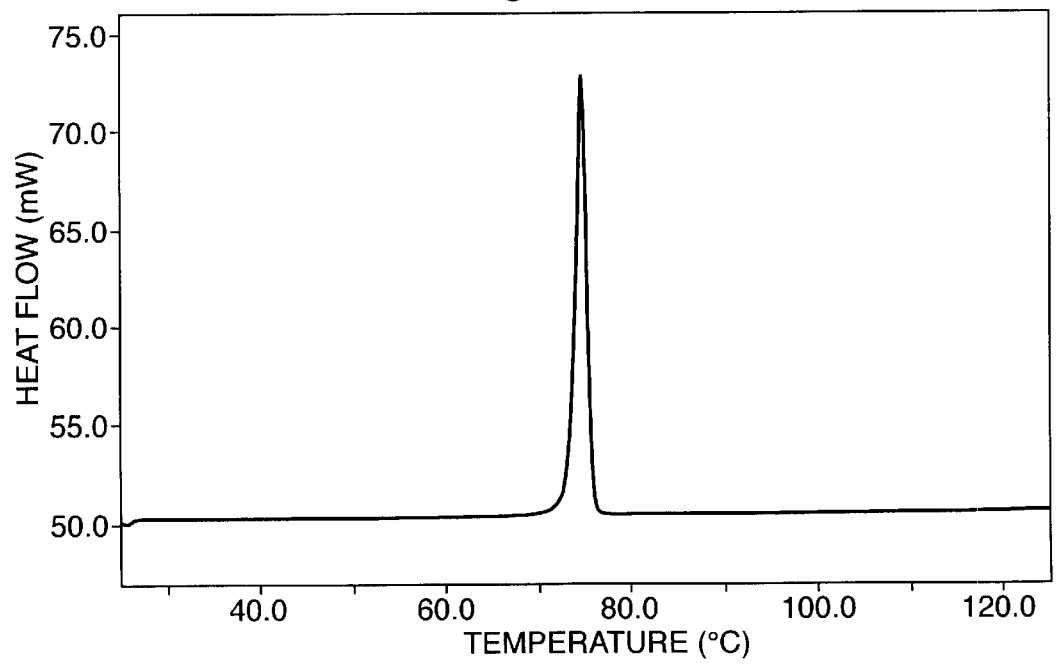

METHODS AND APPARATUS FOR PARTICLE FORMATION

FIELD OF THE INVENTION

This invention relates to the controlled formation of particulate products using supercritical fluids. It provides methods and apparatus for the formation of substances in particulate form, and also particulate products of the methods.

BACKGROUND TO THE INVENTION

It is known to form particles of a substance of interest (a "target substance") by dissolving or suspending it in a suitable vehicle and then using a supercritical fluid anti-solvent to extract the vehicle to cause particle precipitation.

One particular technique for doing this is known as "SEDS" (Solution Enhanced Dispersion by Supercritical fluids). This is described in WO-95/01221 and (in a modified form) in WO-96/00610. The essence of SEDS is that a solution or suspension of a target substance, in an appropriate vehicle, is co-introduced into a particle formation vessel with a supercritical fluid anti-solvent having a relatively high flow rate, in such a way that two things happen substantially simultaneously and substantially immediately on introduction of the fluids into the vessel: the solution or suspension is "dispersed" into separate fluid elements (such as droplets) by the mechanical action of the supercritical fluid (ie, by the transfer of kinetic energy from the supercritical fluid to the solution or suspension), and at the same time the vehicle is extracted from the solution or suspension, again by the supercritical fluid, to cause particle formation.

SEDS allows a high degree of control over conditions such as pressure, temperature and fluid flow rates, and over the physical dispersion of the solution/suspension, at the exact point where particle formation occurs (ie, at the point where the vehicle is extracted into the supercritical fluid). It therefore allows excellent control over the size, shape and other physicochemical properties of the particles formed.

Processes such as SEDS are not however suitable for all types of target substance. If the target is to any degree soluble in the chosen supercritical fluid, then when the supercritical fluid extracts the vehicle it will also dissolve some or all of the target substance. This can lead to reduced product yield, not to mention engineering problems when the solute later precipitates out of the supercritical fluid outside the particle formation vessel.

The same considerations apply to all particle formation processes in which a supercritical fluid is used as an anti-solvent to cause precipitation of a target substance from a solution or suspension. If the substance is at all soluble in the supercritical fluid, whether simply because of the chemical natures of the substance and the fluid (which may also contain modifiers), or because of the particular operating conditions (such as temperature and pressure) being used, problems can arise. Such techniques are thus restricted in application to substances which are poorly soluble or completely insoluble in the chosen supercritical fluid.

A supercritical fluid which is commonly used in particle formation techniques is supercritical carbon dioxide, which is relatively inexpensive, non-toxic and has convenient critical temperature and pressure values. For this particular supercritical fluid, it is generally non-polar or low polarity substances which cause problems, being either very or at least reasonably soluble in it. Thus, for instance, low molecular weight lipophilic materials cannot easily be formed into particles using supercritical carbon dioxide.

In the past, such problems have been overcome either by altering the operating conditions to reduce solubility of the target substance in the supercritical fluid (it is not always possible, however, to alter the conditions sufficiently to achieve that), or by using a different technique altogether for particle formation. A process known as RESS (Rapid Expansion of Supercritical Solution), for instance, may be used to precipitate a substance of interest by dissolving it in a supercritical fluid and then rapidly expanding the resulting solution. However, RESS is generally a less accurate and reliable technique than techniques such as SEDS, allowing less control over the characteristics of the particles formed.

Alternatively, one might attempt to use a different supercritical fluid as the anti-solvent, but it can often be very difficult to select a supercritical fluid which is not only an anti-solvent for the target substance but also capable of dissolving the solvent vehicle—both requirements need to be met for the fluid to be useable. Supercritical nitrogen, for instance, would act as an anti-solvent for the low molecular weight lipophilic materials which cannot be processed using supercritical carbon dioxide, but most conventional organic solvents are insoluble in supercritical nitrogen, so the choice of vehicle would be extremely limited.

It would therefore be advantageous if SEDS, and other similar supercritical fluid particle formation processes, could be modified to be used under conditions where the target substance is soluble in the chosen supercritical fluid. In particular, it would be desirable to be able to use supercritical carbon dioxide in the production of lipophilic and other low polarity materials. The present invention thus aims to facilitate the use of supercritical anti-solvents for an even greater number of target substances, and hence to overcome a technical problem in, and widen the field of application for, an already very useful technology.

STATEMENTS OF THE INVENTION

According to a first aspect of the present invention, there is provided a method for forming particles of a target substance, the method involving:

(a) preparing a solution or suspension of the target substance in a vehicle which is or includes either a near-critical fluid or a first supercritical fluid;

(b) introducing the solution or suspension into a particle formation vessel; and (c) contacting the solution or suspension, in the particle formation vessel, with a second supercritical fluid, under conditions which allow the second supercritical fluid to cause precipitation of particles of the target substance from the solution or suspension;

wherein the second supercritical fluid is miscible or substantially miscible with the vehicle and is a fluid in which the target substance is insoluble or substantially insoluble.

The vehicle should be soluble or at least partially, preferably substantially, soluble in the second supercritical fluid. The fluids can then dissolve in one another by a rapid diffusion process, causing the target substance to "crash out" from its solution or suspension. The second supercritical fluid must not be capable, to any significant degree, of dissolving the substance itself as the particles are formed. In other words, it must be chosen so that the target substance is for all practical purposes insoluble (preferably having a solubility below $10^{-3}$ mole %, more preferably below $10^{-5}$ mole %) in it, under the chosen operating conditions and taking into account any supercritical fluid modifiers present.

By "miscible" is meant generally that the two fluids are miscible in all proportions under the operating conditions used, and "substantially miscible" encompasses the situation where the two fluids can mix sufficiently well, under those operating conditions, as to achieve the same or a similar effect, ie, dissolution of the fluids in one another and precipitation of the target substance.

Using the method of the invention, particles can be formed even of substances which are soluble in a chosen supercritical fluid, by using that supercritical fluid as the vehicle for the substance, and making use of another supercritical fluid (the second supercritical fluid) as the anti-solvent to cause particle precipitation. The target substance is able to dissolve or be suspended in the vehicle, but to precipitate out of it when the vehicle and the second supercritical fluid mix, without product loss into the second supercritical fluid.

In previous literature relating to similar particle formation techniques (such as SEDS), it has never been proposed to use as the vehicle anything other than a conventional solvent, in particular not a solvent which is itself in a supercritical or near-critical condition. However, such vehicles can often have a higher capability for dissolving in the chosen second supercritical fluid than could conventional organic solvents. Accordingly, they enable the use of processes such as SEDS with new types of target substance.

The method of the invention can be used in any situation where the target substance would be too soluble in the chosen (pure or modified) supercritical fluid to initiate particle formation, whether because of the chemical natures of the substance and the fluid or because of the operating conditions used (pressure and temperature, for instance, can significantly affect the solubility of a substance in a supercritical fluid).

The method is in many ways analogous to the SEDS process of particle formation, in that the anti-solvent (the second supercritical fluid) and vehicle mix with and dissolve in one another, causing removal of the vehicle from the target substance. Accordingly, much of the technical information contained in WO-95/01221 and WO-96/00610, as to the execution of SEDS, can also be applicable when carrying out the present invention.

In the following description, the term "supercritical fluid" means a fluid at or above its critical pressure ($P_c$) and critical temperature ($T_c$) simultaneously. In practice, the pressure of the fluid is likely to be in the range between 1.01 and 7.0 of its critical pressure, and its temperature in the range between 1.01 and 4.0 of its critical temperature (in Kelvin). However, some fluids (eg, helium and neon) have particularly low critical pressures and temperatures, and may need to be used under operating conditions well in excess of those critical values, such as up to 200 times the relevant critical value.

Generally, higher temperatures (eg, between about 2 and 4 times the relevant critical temperature) are preferred, particularly for the second supercritical fluid, since they lower the fluid viscosities and can hence improve their dispersing effect on, or dispersion by, the other fluids present. In practice the only real constraint on the fluid temperatures is that they should be below the melting point(s) of the solid substance(s) present, in particular of the target substance.

The term "near-critical fluid" encompasses both high pressure liquids, which are fluids at or above their critical pressure but below (although preferably close to) their critical temperature, and dense vapours, which are fluids at or above their critical temperature but below (although preferably close to) their critical pressure.

By way of example, a high pressure liquid might have a pressure between about 1.01 and 7 times its $P_c$, and a temperature between about 0.5 and 0.99 times its $T_c$. A dense vapour might, correspondingly, have a pressure between about 0.5 and 0.99 times its $P_c$, and a temperature between about 1.01 and 4 times its $T_c$.

The term "vehicle" means a fluid which is able to carry a solid or solids in solution or suspension. A vehicle may be composed of one or more component fluids. In the present invention, the vehicle and the second supercritical fluid should be chosen so that the latter can act, under the operating conditions used, to reduce the capability of the vehicle to carry the target substance, when the two fluids come into contact.

The term "supercritical solution" means a solution of a substance and/or another fluid, in a supercritical fluid, the solution itself being in a supercritical state. The term "near-critical solution" means a solution, itself in a near-critical state, of a substance and/or fluid in a near-critical fluid.

The terms "disperse" and "dispersion" refer generally to the transfer of kinetic, energy from one fluid to another. They usually imply the formation of droplets, or of other analogous fluid elements, of the fluid to which the kinetic energy is transferred, typically of the solution or suspension of the target substance and/or of the vehicle.

The target substance may be any substance which needs to be produced in particulate form. It may be a substance for use in or as a pharmaceutical. However, it may also be a material of use in the ceramics, explosives or photographic industries; a foodstuff; a dye; a coating; etc. It may be organic or inorganic, monomeric or polymeric. In each case, the principle behind the method of the invention remains the same; the technician need only adjust operating conditions and choose appropriate fluids in order to effect proper control over the particles being formed.

The target substance may be in a single or multi-component form. The particulate product formed from the substance may also be in a multi-component form it could for instance comprise an intimate mixture of two materials, or one material in a matrix of another, or one material coated onto a substrate of another, or other similar mixtures. Such products may be made from solutions or suspensions containing only single component starting materials (more than one solution/suspension, not all of which need contain a supercritical or near-critical fluid vehicle, may be introduced into the particle formation vessel with the second supercritical fluid). The particulate product may also be a substance formed from an in situ reaction (ie, immediately prior to, or on, the solution/suspension contacting the second supercritical fluid) between two or more reactant substances, each carried by an appropriate vehicle. To produce such multi-component products, the second supercritical fluid may itself be used to carry a component such as a reactant or a carrier material, intended to be incorporated into the final product.

Modifications involving the use of in situ reactions and/or more than one solution or suspension of a target substance, are described in connection with SEDS in WO-95/01221 and WO-96/00610, and can also be applied when carrying out the present invention.

The target substance will typically be non-polar or of fairly low polarity, in which case the vehicle should also be of low polarity and the second supercritical fluid may have a relatively high polarity. However, the reverse may also apply, ie, polar target substance with polar vehicle and relatively low polarity second supercritical fluid.

The vehicle is preferably, although not necessarily, a supercritical fluid. It may for instance be carbon dioxide, nitrogen, nitrous oxide, sulphur hexafluoride, xenon, ethylene, chlorotrifluoromethane, ethane or trifluoromethane, in an appropriate condition with respect to its $P_c$ and $T_c$. A particularly preferred vehicle is carbon dioxide ($P_c$=74 bar; $T_c$=31° C.), preferably supercritical carbon dioxide. The choice naturally depends on the target substance; in the case of low polarity or non-polar substances, in particular low molecular weight lipophilic substances, supercritical carbon dioxide is again an appropriate vehicle.

The vehicle may include more than one supercritical or near-critical fluid, and/or other fluids such as conventional solvents, provided that it has, overall, the necessary solubility properties vis-a-vis the target substance and the second supercritical fluid. It may optionally contain one or more modifiers or co-solvents. A modifier (or co-solvent) may be described as a chemical which, when added to a fluid such as a supercritical or near-critical fluid, changes the intrinsic properties of that fluid at or around its critical point, in particular its ability to dissolve other materials. Suitable modifiers include water, and conventional organic solvents such as methanol, ethanol, isopropanol or acetone. When used, a modifier preferably constitutes not more than 40 mole %, more preferably not more than 20 mole %, and most preferably between 1 and 10 mole %, of the vehicle.

The choice of vehicle in any particular case will depend on the nature of the target substance, on the second supercritical fluid and on other practical criteria including those governing the desired end product. The target substance is preferably soluble in the vehicle, preferably having a solubility in the vehicle of $10^{-4}$ mole % or greater, under the chosen operating conditions (pressure, temperature and modifiers present).

The second supercritical fluid may be for instance supercritical carbon dioxide, nitrogen, nitrous oxide, helium, sulphur hexafluoride, xenon, ethylene, chlorotrifluoromethane, ethane, trifluoromethane or a mixture of any of these. A convenient second supercritical fluid is supercritical nitrogen ($P_c$=33.9 bar; $T_c$=minus 147° C.), which is an anti-solvent for many solids, including many non-polar or low polarity substances. Supercritical noble gases, for example helium, can also be effective anti-solvents for many target substances.

The use of supercritical or near-critical carbon dioxide as the vehicle and nitrogen as the second supercritical fluid is particularly effective, since supercritical nitrogen is miscible with, and can readily dissolve, supercritical carbon dioxide.

The second supercritical fluid may also contain one or more modifiers, of the same general type and in the same proportions as can the vehicle. As mentioned above, it may contain further target substances or reactants for introduction into the particle formation vessel.

The choice of suitable operating conditions to allow particle precipitation to occur will be well within the capabilities of the person skilled in this art. Generally, the conditions in the particle formation vessel must be such that the second supercritical fluid remains in the supercritical state whilst in the vessel. The fluid mixture formed when the solution/suspension comes into contact with the second supercritical fluid should also, for at least one of its constituent fluids (usually the second supercritical fluid, which in general will be the major constituent of the mixture), be in a supercritical state at the time of particle formation. The mixture should at that time comprise a single-phase mixture of the vehicle and the second supercritical fluid, otherwise the particulate product might be distributed between two or more fluid phases, in some of which it might be able to redissolve. This is why the second supercritical fluid needs to be miscible or substantially miscible with the vehicle.

The pressure and temperature inside the particle formation vessel may be the same as or different to those of the solution or suspension about to be introduced into it.

Under these conditions, particle precipitation will generally be immediate, or effectively immediate, when the solution/suspension and the second supercritical fluid come into contact. This allows tile rapid formation of pure, dry particulate products. The exact pressures and temperatures needed to achieve this situation depend of course on the nature of the second supercritical fluid and on the target substance, the vehicle and any other fluids being used.

The method by which the solution or suspension and the second supercritical fluid are introduced into the particle formation vessel may be analogous to that used in SEDS, or in a modified version thereof, such as is described in WO-95/01221 or WO-96/00610.

Thus, the solution or suspension and the second supercritical fluid may be co-introduced into the particle formation vessel through a fluid inlet means which allows the second supercritical fluid (physically) to mix and disperse the solution or suspension, at the same time as it (chemically) causes precipitation from it. This can provide a very high degree of control over the particles formed.

To achieve this, the fluid inlet means may allow both the solution/suspension and the second supercritical fluid to enter the particle formation vessel at the same or substantially the same point, which is also the same as, or substantially the same as, the point where they meet. Preferably, the inlet means is so arranged that the second supercritical fluid can act, at that same point or substantially that same point, to facilitate intimate mixing of the fluids, and preferably to break up the solution/suspension into individual fluid elements (the precursors to the eventual particles), by the transfer of kinetic energy from the second supercritical fluid to the solution/suspension. Preferably, particle precipitation is allowed to occur at or substantially at the point where the two fluids enter the particle formation vessel.

The fluid inlet means may be of the type which allows "pre-filming" or "sheathing" of at least one of the fluids to occur, immediately prior to its dispersion by an impinging flow of another fluid introduced through the inlet means. For instance, the inlet means can be used to cause pre-filming of the solution or suspension immediately prior to its dispersion by the second supercritical fluid. This means that the dimensions of the inlet passages of the inlet means, and the relative positions of their outlets, must be such that a fluid entering through one passage is formed, as it reaches the outlet of that passage, into a thin film or sheath, by its contact with, say, the lip of an adjacent passage outlet. This film or sheath can then be stretched, and ultimately dispersed into separate fluid elements, when it comes into contact with an oncoming stream of a fluid in another inlet passage. Clearly, the thickness of the film or sheath, and hence the sizes of the fluid elements formed on dispersion, will depend to a large extent on the relative flow rates of the fluids, and also on the inlet passage dimensions.

In one embodiment of the invention, the second supercritical fluid and the solution or suspension are co-introduced into the particle formation vessel with concurrent directions of flow, preferably with coaxial or substantially coaxial flows, such as using a multi-passage coaxial nozzle. Such a nozzle has an outlet end communicating with the interior of the particle formation vessel, and two or more coaxial, conveniently concentric, passages which terminate adjacent or substantially adjacent one another at the outlet end, at least one of the passages serving to introduce a flow of the second supercritical fluid into the particle formation vessel, and at least one of the passages serving to introduce a flow of the solution or suspension.

Aspects of such a coaxial nozzle may be as described in WO-95/01221 and WO-96/00610. For instance, the opening at the outlet end (tip) of the nozzle will preferably have a diameter in the range of 0.005 to 5 mm, more preferably 0.05 to 2 mm, most preferably between 0.1 and 0.5 mm, for instance about 0.1, 0.2, 0.3 or 0.35 mm. The angle of taper of the outlet end (with respect to the longitudinal axis of the nozzle) will depend on the desired velocity of the fluids introduced through the nozzle; a change in the angle may be used, for instance, to increase the velocity of the second supercritical fluid and hence to increase the amount of its physical contact with the solution/suspension, leading to more efficient fluid mixing. Typically, the angle of taper will be in the range 10° to 60°, preferably between 10° and 50°, more preferably between 20° and 40°, and most preferably about 30°. Alternatively, the outlet need not be tapered at all.

The nozzle may be made of any appropriate material, for example stainless steel. It may have any appropriate number of coaxial passages (preferably two or three), some of which may be used to introduce additional reagents into the particle formation vessel. One or more of the passages may be used to introduce two or more fluids at the same time, and the inlets to such passages may be modified accordingly.

The internal diameters of the coaxial passages may be chosen as appropriate for any particular case. Typically, for a three-passage nozzle, the ratio of the internal diameters of the outer and the inner passages may be in the range from 2 to 10, preferably between 2 and 5, more preferably between 3 and 4. The ratio of the internal diameters of the outer and intermediate passages may be in the range from 1.01 to 5, preferably between 1.2 and 3. For a two-passage nozzle, the ratio of the internal diameters of the outer and inner passages may be in the range from 1 to 10, preferably between 2 and 6, more preferably between 2 and 4.

The outlets of two or more of the passages may be relatively staggered along the longitudinal axis of the nozzle, ie, one passage may terminate slightly (preferably between about 0.05 and 10 mm, more preferably between about 0.05 and 1 mm) upstream or downstream, in use, of another. For instance, the outlet of an inner passage may terminate slightly upstream of that of a surrounding passage, to allow a degree of internal mixing between fluids introduced through the two passages.

The use of such coaxial nozzles as the fluid inlet means can minimise contact between the formed particles and the vehicle in the region of the inlet means, which contact could reduce control of the final product size, shape and yield. Extra control over the size of the dispersed vehicle fluid elements, in addition to that provided by the design of the inlet means, may be achieved by controlling the flow rates of the second supercritical fluid and the solution/suspension into the particle formation vessel.

In the method of the invention, however, co-introduction of the fluids into the particle formation vessel is not essential. The solution/suspension and the second supercritical fluid may be introduced through separate inlet means and/or at different locations in the vessel, and/or at different angles to one another. They may even be introduced into the vessel at different times. All that is needed is that they come into contact with each other under conditions which allow the second supercritical fluid to cause particles to precipitate out of the solution/suspension. Ideally, however, they are introduced in a way which ensures efficient fluid mixing immediately prior to, and at, the point of particle formation, and the fluid inlet means is/are preferably designed to assist in this.

In the method of the invention, the relative flow rates of the fluids introduced into the particle formation vessel may be used to influence the characteristics, in particular the size and/or size distribution, of the particles formed. This is particularly relevant when using the action of the second supercritical fluid to disperse the solution or suspension. Preferably, the flow rate of the second supercritical fluid, measured at or immediately prior to its contact with the solution or suspension, is higher than that of the solution or suspension—this can lead to the formation of generally smaller fluid elements (eg, droplets) of the solution or suspension, and hence relatively small particles, having a narrow size distribution, when the second supercritical fluid causes precipitation out of the fluid elements.

In some cases, the flow rate of the second supercritical fluid might be up to 100 times greater than that of the solution or suspension, preferably between 5 and 30 times greater, more preferably between 10 and 20 times greater. (These figures again refer to fluid flow rates measured at or immediately prior to the fluids coming into contact with one another.) It will in general be chosen to ensure an excess of the second supercritical fluid over the vehicle when the fluids come into contact, to minimise the risk of the vehicle re-dissolving and/or agglomerating the particles formed. At that point, the amount of the second supercritical fluid relative to that of the vehicle must naturally be sufficient to cause particles of the target substance to precipitate from the solution or suspension. Typically, the vehicle may constitute between 1 and 80 mole %, preferably between 1 and 20 mole %, more preferably between 1 and 5 mole %, of the fluid mixture formed.

The method thus preferably involves controlling the flow rate of one or more of the fluids to influence the characteristics of the particulate product. The flow rate of the solution/suspension, as well as that of the second supercritical fluid, may affect these characteristics.

The flow rates of the second supercritical fluid and the solution or suspension, together with the concentration of the target substance in its solution or suspension, are ideally selected so as to minimise the risk of particle precipitation in, and hence blockage of, the fluid inlet means or other upstream apparatus parts. For the same reason, back-flow of the second supercritical fluid, into the supply line for the solution/suspension, is also ideally reduced or eliminated. This may be done for instance by installing a one-way valve in the solution/suspension supply line, upstream of and preferably immediately before the point of contact between the second supercritical fluid and the solution suspension. Instead or in addition, the supplied pressure of the solution or suspension, to the particle formation vessel, may be maintained in excess of that of the second supercritical fluid. It is also preferable to maintain the temperature of the solution or suspension, prior to its introduction into the particle formation vessel, in excess of that of the second supercritical fluid.

The fluids are ideally introduced into the particle formation vessel with a smooth, continuous and preferably pulse-less or substantially pulse-less flow. This again helps prevent draw-back of fluids. Conventional apparatus may be used to ensure such fluid flows.

The densities of the fluids used will depend on the operating conditions, which in turn will be selected according to the natures of the species present and of the desired end product. In the case where supercritical carbon dioxide is used as the vehicle, its density might typically be between 0.1 and 0.9 g/ml. Supercritical nitrogen might typically be used as the second supercritical fluid at a density of between 0.01 and 0.05 g/ml, preferably around 0.02 g/ml.

Depending on the nature of the target substance, two main embodiments of the method of the invention are likely to be preferred:

a) where the target substance is highly soluble, preferably freely soluble in the vehicle, it is dissolved directly in the vehicle and the resultant solution is then introduced into the particle formation vessel to contact the second supercritical fluid. In order to dissolve the substance in the vehicle, it is preferably charged into a vessel through which a flow of the vehicle is passed to form a saturated solution.

b) where the target substance is less than freely soluble in a chosen vehicle, a solution of the substance may firstly be made up using another ("primary") solvent in which it is more soluble. This solution is then itself dissolved in or mixed with the chosen vehicle, for instance by dispersing the solution into a fluid mixing vessel together with the vehicle (this dispersion process may also be carried out using an inlet means of the type suitable for use in the particle formation step of SEDS). The resulting supercritical or near-critical solution is then contacted with the second supercritical fluid in the particle formation vessel.

When using embodiment (a), the target substance can preferably form a stable single-phase solution in the vehicle, at a target substance vehicle weight ratio of at least 1:1, under the relevant operating conditions. The embodiment may however be used for less soluble target substances, perhaps even at solubilities as low as $10^{-4}$ mole %, provided sufficient time can be allowed for their dissolution in the vehicle.

For embodiment (b), the solubility of the target substance in the vehicle, under the relevant operating conditions, may typically be less than about $10^{-2}$ mole %, possibly less than about $10^{-4}$ mole %. Embodiment (b) may also of course be used for target substances which are freely soluble in the chosen vehicle.

In embodiment (b), the "vehicle" is effectively, at the time of particle formation, the initially chosen fluid plus the primary solvent (which can also be seen as the chosen fluid plus a modifier). The embodiment could be of use where the target substance, although only slightly soluble in a chosen fluid, is much more soluble in that fluid when a few volume percent of a modifier has been added to it. The "vehicle" need only be in a supercritical or near-critical state at the point where it contacts the second supercritical fluid, and not necessarily at the point where it is mixed with the primary solvent.

The present invention also provides, according to a second aspect, apparatus for use in carrying out the above described embodiment (b). This apparatus includes a particle formation vessel; means for controlling the temperature and pressure in the particle formation vessel at desired levels; a fluid mixing vessel; means for controlling the temperature and pressure in the fluid mixing vessel at desired levels; first fluid inlet means for introducing into the fluid mixing vessel a vehicle and a solution of a target substance in a primary solvent, so as to form in the fluid mixing vessel a solution of the target substance and the primary solvent in the vehicle; and second fluid inlet means for introducing the solution thus formed, preferably together with a second supercritical fluid, into the particle formation vessel.

Each of the first and second fluid inlet means may be of the type described in connection with the first aspect of the invention.

According to a third aspect of the present invention, there is provided a particulate product formed using the method of the first aspect.

The invention will now be described by way of example only, with reference to the accompanying illustrative drawings, of which:

FIGS. 3–6 are particle size distribution curves for products obtained in accordance with the invention (see experimental Examples 1a, 1b, 1c and 2);

FIGS. 7 and 8 are DSC (differential scanning calorimetry) profiles for the starting material and the product respectively of Example 1a;

DETAILED DESCRIPTION

Figure 1:
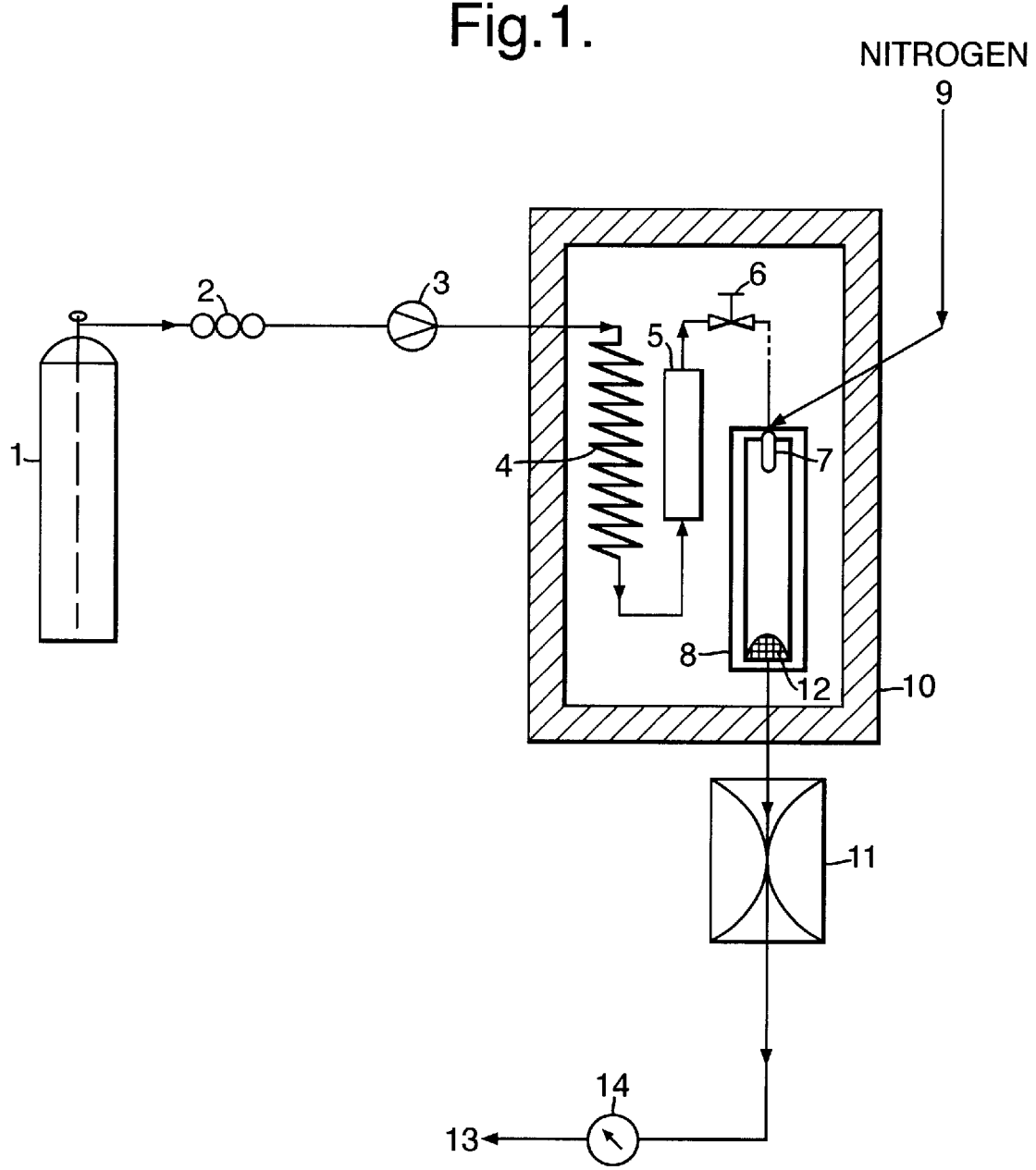
FIG. 1 illustrates schematically how a method in accordance with the first aspect of the invention may be carried out.

FIG. 1 shows, schematically only, how a method according to the invention may be carried out. In the example described, the vehicle used is supercritical carbon dioxide, and the second supercritical fluid is supercritical nitrogen. The target substance is soluble in supercritical carbon dioxide.

Carbon dioxide from source 1 is passed through cooler 2, pump 3 and heat exchanger 4, to take it into its supercritical state. It then passes through sample vessel 5, containing a target substance from which particles are to be formed. The target substance has been charged into the vessel 5 with glass beads, to form a bed exposing as high as possible a surface area to the supercritical carbon dioxide, and also to eliminate the risk of channelling of the carbon dioxide.

The carbon dioxide dissolves the substance and the resulting solution passes, via pressure regulator 6, through a two-component inlet nozzle 7 into particle formation vessel 8.

Supercritical nitrogen is also fed into the vessel 8 via nozzle 7, as shown at 9. The pressure and temperature inside vessel 8 are controlled by means of surrounding oven 10 and automated back pressure regulator 11.

At the nozzle outlet, the supercritical nitrogen contacts the solution of the target substance in supercritical carbon dioxide, dissolves in the carbon dioxide and causes precipitation of particles of the target substance, which collect in the particle retaining device (such as a filter or cyclone) 12. Supercritical conditions are maintained in the vessel, allowing the fluids (ie, a supercritical mixture of carbon dioxide and nitrogen) to be removed to vent 13, via the back pressure regulator 11 and a flow meter 14.

The nozzle 7 preferably has two coaxial passages, one for introduction of the carbon dioxide/target substance solution, and one for introduction of the supercritical nitrogen. It preferably allows these two fluids to be introduced into the vessel with concurrent directions of flow, in such a way that they meet and enter the vessel at substantially the same point, and preferably also in such a way that the mechanical energy of the supercritical nitrogen contributes to the efficient mixing of the two fluids at their point of contact.

In carrying out the invention according to FIG. 1, it is desirable to form a saturated solution of the target substance in the supercritical vehicle prior to introducing the solution into the particle formation vessel. The flow rate of the second supercritical fluid should be high with respect to that of the vehicle/target substance solution.

Figure 2:
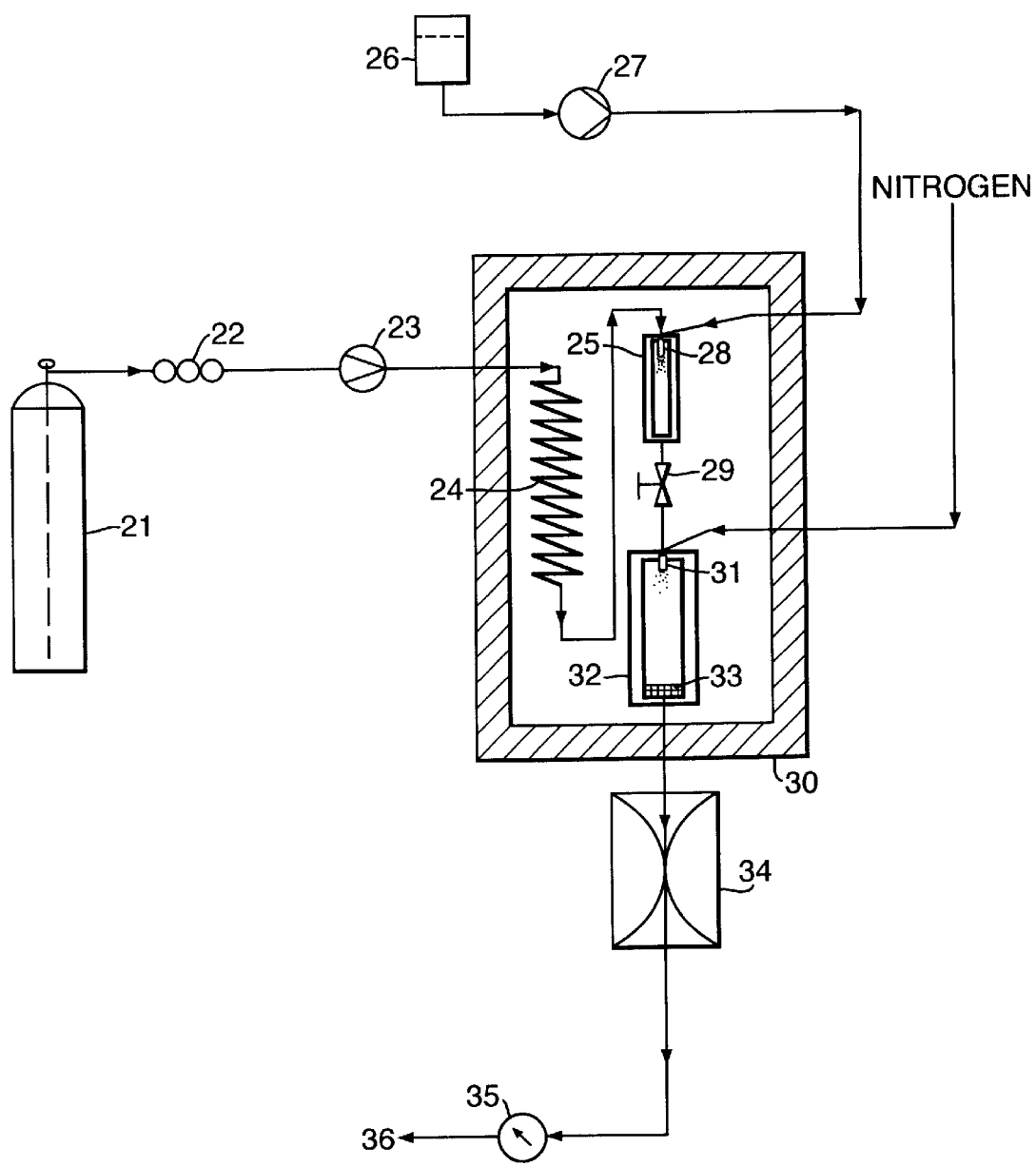
FIG. 2 illustrates schematically how an alternative method may be carried out in accordance with the invention.

The apparatus shown schematically in FIG. 2 is for use in producing particles of a target substance which is less than freely soluble in the chosen vehicle but much more soluble in the vehicle once modified with another solvent. For instance, a slightly polar target substance might not be highly soluble in supercritical carbon dioxide, but much more soluble in a mixture of supercritical carbon dioxide and a few mole percent of a polar modifier.

In the FIG. 2 system, the vehicle (in this example carbon dioxide) is fed from source 21 through cooler 22, pump 23 and heat exchanger 24, to bring it into a supercritical state. It is then fed into a mixing vessel 25, together with a solution of the target substance in an appropriate primary solvent (from source 26, via pump 27). The solution and the supercritical carbon dioxide enter the mixing vessel through a two-passage coaxial nozzle 28, of the type described above, which allows the kinetic energy of the carbon dioxide to act to disperse the solution, ensuring thorough mixing of the two fluids when they meet at the nozzle outlet. This yields a solution of the target substance in the carbon dioxide and the primary solvent, ie, effectively a solution of the target substance in modified supercritical carbon dioxide. The "modified" solution is maintained in a supercritical state by controlling the pressure and temperature inside the mixing vessel, using pressure regulator 29 and surrounding oven 30.

The supercritical solution then passes to a second nozzle 31, through which it is co-introduced into a particle formation vessel 32 with a second supercritical fluid flowing with a relatively high flow rate. Nozzle 31 is of the same general form as nozzle 28. At the same time, or substantially the same time, as the fluids meet and enter the vessel, the second supercritical fluid dissolves in the carbon dioxide vehicle, reduces its capacity for the target substance and thus causes precipitation of particles which can be collected in the particle retaining device 33. Again, supercritical conditions are maintained in the vessel 32 using back pressure regulator 34 and the oven 30.

The fluid mixture which remains after particle precipitation can be vented at the bottom of the particle formation vessel 32, via flow meter 35.

If difficulties arise in pumping low boiling point liquefied gases such as liquefied nitrogen, it may be convenient, at least for the laboratory scale, to use gas pumps or cylinders providing an appropriate level of pressure. The gases can simply be vented from their higher pressure cylinders into the particle formation vessel which is at a lower pressure. Their flow can be controlled by a needle valve. Cryogenic pumps may also be used if the circumstances warrant.

It is important to keep the rate of fluid addition as constant as possible and to achieve efficient fluid mixing throughout the particle formation process. To acquire good control over the rate of addition of, for instance, supercritical nitrogen under high pressures, gas cylinders or boosters may be used. Of these, motor driven gas boosters tend to be more effective than high pressure gas cylinders, since they can offer:

higher operation pressures and flow outputs;

better control over flow rates (high pressure cylinders suffer from continuous pressure drop during operation and a bank of cylinders is often needed to compensate for this pressure reduction during a long particle formation procedure); and longer fluid delivery times.

Laboratory scale gas boosters are available from, for instance, Stansted Power Fluid Ltd (Essex, UK) and can deliver up to 40 standard litres per minute at pressures exceeding 350 bar.

EXPERIMENTAL EXAMPLES

The following examples demonstrate how the method of the present invention may be used to produce a range of target materials, some of which would be incompatible with a conventional SEDS process, whilst allowing a high degree of control over the product properties.

Example 1

This experiment made use of the system described in connection with FIG. 1. The drug ibuprofen was the target substance, chosen for its high solubility in both pure and modified supercritical carbon dioxide. The vehicle was supercritical carbon dioxide and the second supercritical fluid was supercritical nitrogen. The method of the invention was used to produce particles of the drug (Example 1a) and to control the size of those particles by varying the flow rates of the fluids involved (Examples 1b and 1c).

Example 1a 1g of ibuprofen was mixed with glass beads (200–300 micron, acid washed (Sigma, UK)) and introduced into a 10 ml Keystone vessel (the sample vessel 5) to form a uniform bed. The bed was sandwiched between two filters (average pore size 2 microns) to eliminate the risk of physical entrainment of drug particles in the carbon dioxide flow. The sample vessel was provided with a pressure regulator independent of that of the particle formation vessel 8.

The fluids were introduced into the particle formation vessel using a two-passage coaxial nozzle of the preferred type described above, having a 0.1 mm diameter outlet. The nozzle ensured thorough mixing of the fluids at their point of contact, ie, at their point of entry into the vessel. The conditions in the vessel were such that particle formation occurred simultaneously, or substantially so, on the fluids meeting and entering the vessel.

1 ml/min of carbon dioxide (measured at the pump head) was pumped into the sample vessel containing the ibuprofen bed, which was maintained at 130 bar. The resultant supercritical solution, at the same flow rate, was introduced into the particle formation vessel via the outer passage of the nozzle, and supercritical nitrogen was introduced through the inner passage. The nitrogen flow rate, measured at the flow meter 14 (ie, after the back pressure regulator) at ambient conditions, was kept constant through all experiments at 10 l/min.

The pressure inside the particle formation vessel (a 50 ml Keystone vessel) was set at 60 bar. The oven temperature was 40° C.

At the end of the experiment a fine, fluffy white powder was collected in the retaining device 12 and stored free from moisture for subsequent analysis.

Figures 3, 4:
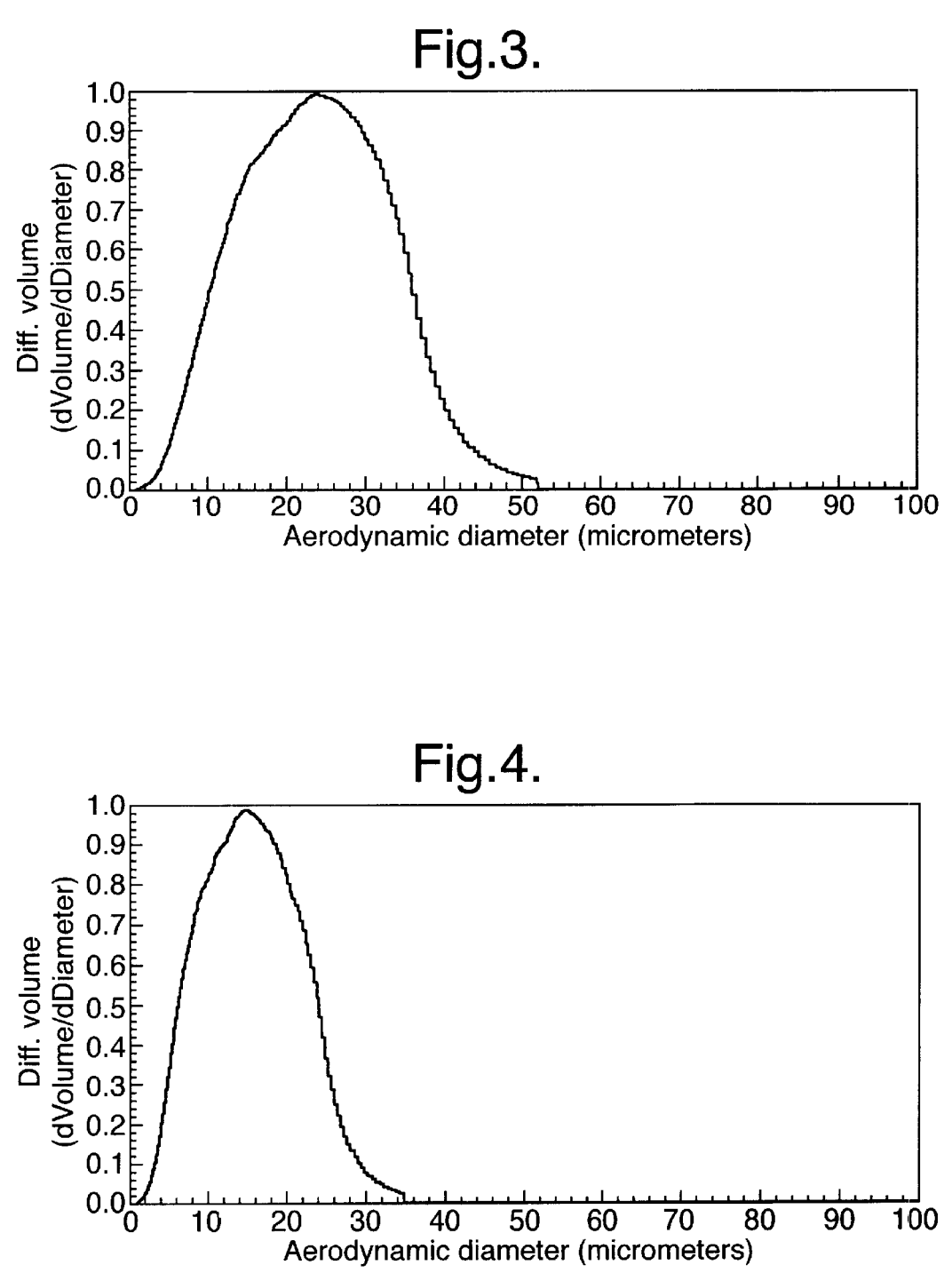

Particle size analysis of the product was carried out using the Aerosizer/Aerodisperser system (API, USA). The results, in the form of a particle size distribution curve, are shown in FIG. 3 and summarised in Table 1 below. The mean particle diameter, by volume, was about 21 micron.

TABLE 1

| % UNDER | SIZE | % UNDER | SIZE |
|---|---|---|---|
| 5% | 9.241 | 55% | 24.87 |
| 10% | 11.68 | 60% | 26.16 |
| 15% | 13.57 | 65% | 27.48 |
| 20% | 15.21 | 70% | 28.83 |
| 25% | 16.74 | 75% | 30.25 |
| 30% | 18.21 | 80% | 31.76 |
| 35% | 19.62 | 85% | 33.44 |
| 40% | 20.99 | 90% | 35.44 |
| 45% | 22.30 | 95% | 38.65 |
| 50% | 23.58 | | |
| Mean size: | | 21.68 | |
| Standard deviation: | | 1.569 | |

Example 1b

Example 1a was repeated, but with the carbon dioxide flow rate increased from 1 to 4 ml/min (at the pump head). All other operating conditions remained the same.

The product was a fine fluffy white powder. Analysis using the Aerosizer/Aerodisperser system yielded the particle size distribution curve shown in FIG. 4 and summarised in Table 2. The mean particle diameter, by volume, was about 14 micron.

TABLE 2

| % UNDER | SIZE | % UNDER | SIZE |
|---|---|---|---|
| 5% | 5.920 | 55% | 16.18 |
| 10% | 7.411 | 60% | 17.07 |
| 15% | 8.631 | 65% | 17.99 |
| 20% | 9.720 | 70% | 18.94 |
| 25% | 10.75 | 75% | 19.95 |
| 30% | 11.72 | 80% | 21.05 |
| 35% | 12.66 | 85% | 22.25 |
| 40% | 13.56 | 90% | 23.67 |
| 45% | 14.43 | 95% | 25.84 |
| 50% | 15.30 | | |
| Mean size: | | 14.12 | |
| Standard deviation: | | 1.586 | |

Example 1c

Figures 5, 6:
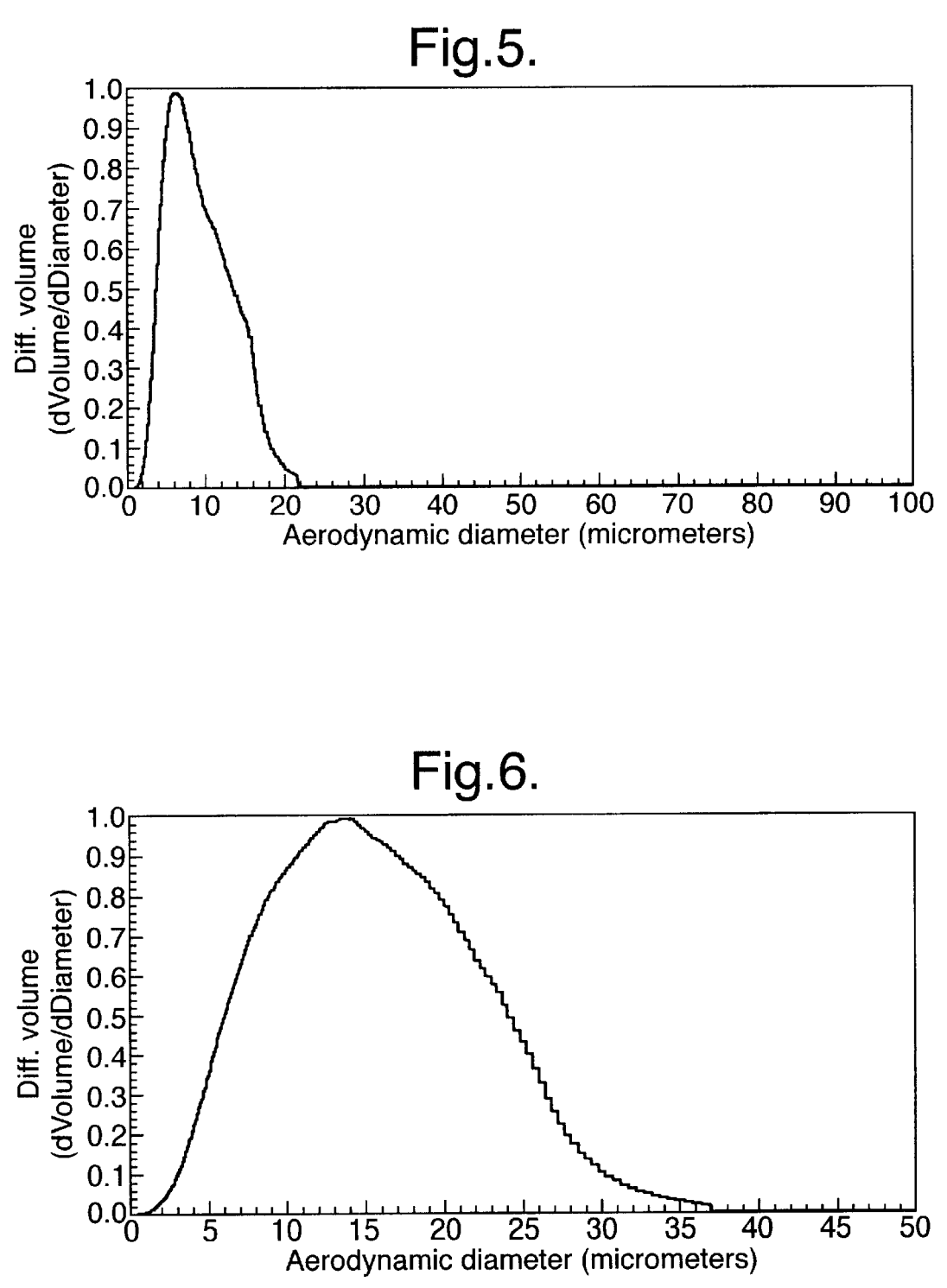

Again Example 1a was repeated, but this time with a carbon dioxide flow rate of 8 ml/min (at the pump head). The product was again a fine fluffy white powder, which when analysed (see FIG. 5 and Table 3) showed a mean particle diameter, by volume, of about 8 micron.

TABLE 3

| % UNDER | SIZE | % UNDER | SIZE |
|---|---|---|---|
| 5% | 3.762 | 55% | 9.186 |
| 10% | 4.462 | 60% | 9.849 |
| 15% | 5.018 | 65% | 10.55 |
| 20% | 5.518 | 70% | 11.28 |
| 25% | 5.999 | 75% | 12.06 |
| 30% | 6.479 | 80% | 12.92 |
| 35% | 6.966 | 85% | 13.88 |

TABLE 3-continued

| 40% | 7.471 | 90% | 14.96 |
|---|---|---|---|
| 45% | 8.004 | 95% | 16.35 |
| 50% | 8.572 | | |
| Mean size: | | 8.333 | |
| Standard deviation: | | 1.589 | |

Example 1

Conclusions

Figure 9:
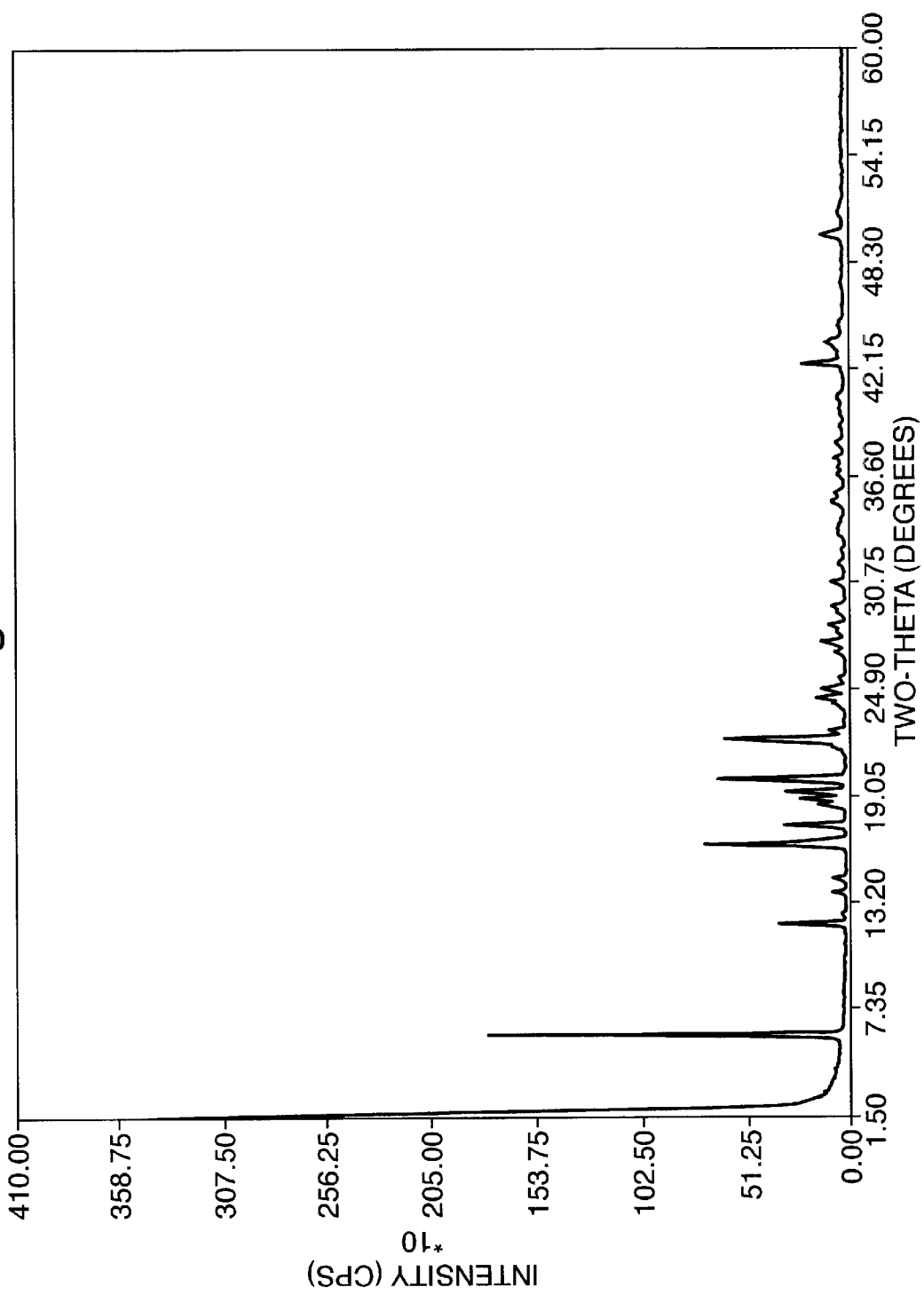
FIGS. 9–13 are XRPD (X-ray powder diffraction) patterns for, respectively, the starting material and the product of Example 1a, the products of Examples 3a and 3b and the product of Example 4.
Figure 10:
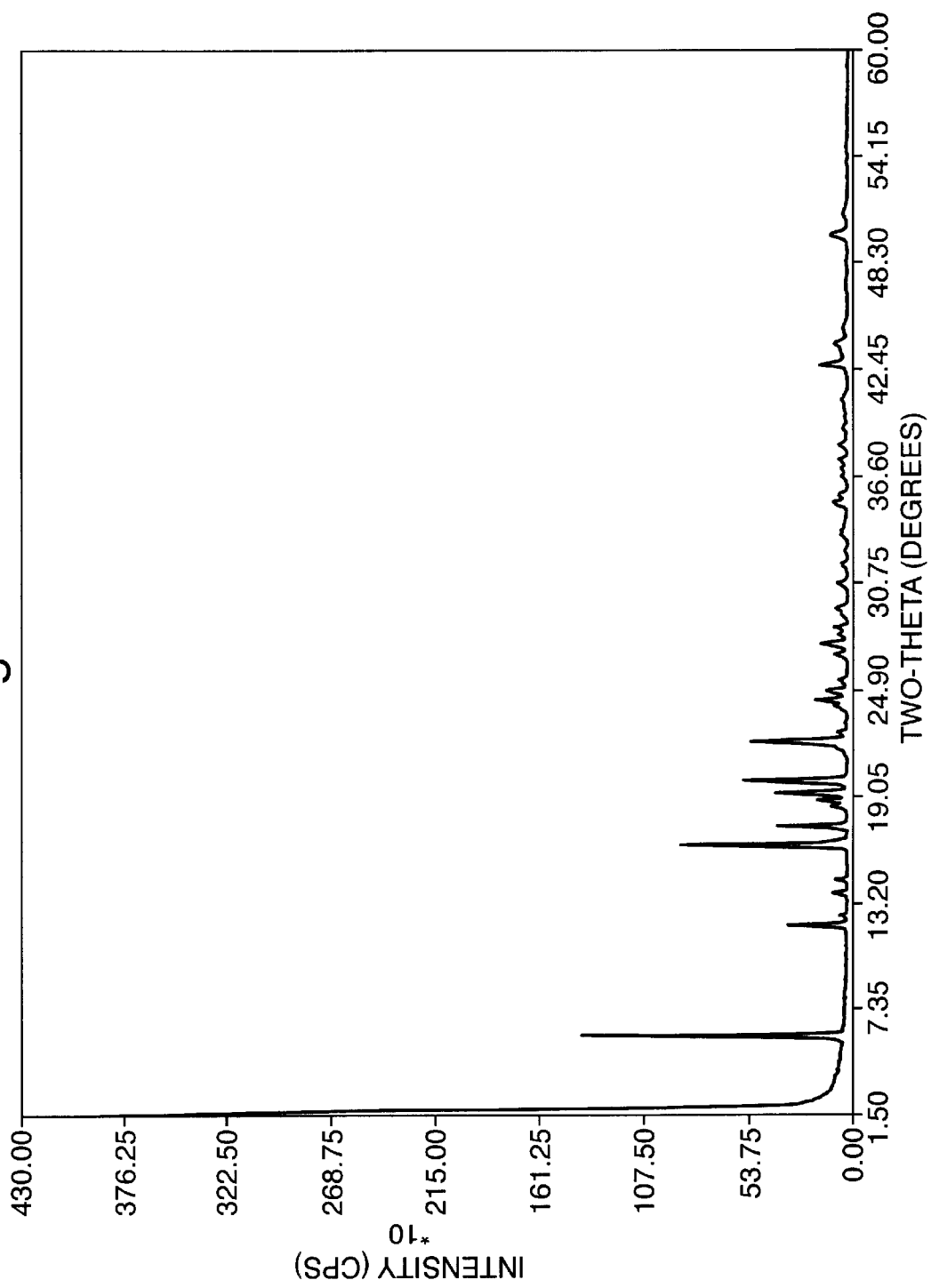

These experiments show that varying the flow rate of the vehicle, in which the target substance is dissolved, can be used to influence the size of particulate products made according to the invention. Here, increasing the flow rate led to reduced particle sizes.

Example 2

This experiment made use of the system described in connection with FIG. 2. Ibuprofen was dissolved in a conventional solvent (methanol) prior to introduction of the supercritical carbon dioxide vehicle. Supercritical nitrogen was used to cause particle precipitation.

A 10% w/v solution of ibuprofen in methanol was pumped at 0.05 ml/min into the mixing vessel 25 via the two-passage coaxial nozzle 28, together with supercritical carbon dioxide at a flow rate of 4 ml/min (measured at the pump head). The nozzle outlet had a diameter of 0.2 ml/min. The mixing vessel (24 ml, Keystone) was kept at 150 bar and 40° C.

The resultant solution, mixed and dispersed by the action of the supercritical carbon dioxide, was then fed to the particle formation vessel 32 (50 ml, Keystone), via the inner passage of another two-component nozzle 31, this time with a 0.1 mm diameter outlet. Supercritical nitrogen was introduced through the outer passage of the same nozzle, with a flow rate (measured at ambient temperature) of 10 l/min.

The product was a fine fluffy white powder, collected in the vessel 32. Analysis using the Aerosizer revealed (see FIG. 6 and Table 4) a mean particle diameter, by volume, of about 14 micron.

TABLE 4

| % UNDER | SIZE | % UNDER | SIZE |
|---|---|---|---|
| 5% | 5.815 | 55% | 16.10 |
| 10% | 7.327 | 60% | 17.06 |
| 15% | 8.537 | 65% | 18.06 |
| 20% | 9.612 | 70% | 19.10 |
| 25% | 10.62 | 75% | 20.20 |
| 30% | 11.57 | 80% | 21.41 |
| 35% | 12.49 | 85% | 22.79 |
| 40% | 13.38 | 90% | 24.42 |
| 45% | 14.26 | 95% | 26.78 |
| 50% | 15.17 | | |
| Mean size: | | 14.13 | |
| Standard deviation: | | 1.611 | |

Polymorphic Form of the Products

The products of Examples 1 and 2, when examined using DSC (differential scanning calorimetry) and XRPD (X-ray powder diffraction) techniques, were all found to be of the same polymorphic form as the starting material. By way of demonstration, FIG. 7 is a DSC profile for the ibuprofen used as the starting material; FIG. 8 is a DSC profile for the product of Example 1a. FIGS. 9 and 10 are XRPD spectra for the starting material and the product of Example 1a respectively.

These data show that the methods of the present invention may be used to form particles of target substances without compromising their purity or their crystalline form.

Example 3

In this experiment, the system described in connection with FIG. 2 was used to prepare particulate salicylic acid, which is soluble in supercritical carbon dioxide provided a small amount of a polar modifier is also present. Particle formation was carried out using two different salicylic acid solutions as the starting materials (Examples 3a and 3b).

Example 3a

A 3% w/v solution of salicylic acid in methanol was introduced at a flow rate of 0.2 ml/min into the mixing vessel 25 (in this case, a 5 ml Keystone vessel), via the inner passage (internal diameter 0.15 mm, external diameter 0.30 mm) of a two-passage coaxial nozzle. Supercritical carbon dioxide was introduced through the outer passage (internal diameter 0.35 mm) at a flow rate of 9 ml/min measured at the pump head. The nozzle outlet diameter was 0.35 mm, and the outlet of the inner passage terminated 0.2 mm upstream of that of the outer passage. The mixing vessel was maintained at 200 bar and 50°C.

Since the solubility of the acid in the supercritical fluid increases dramatically in the presence of a few percent of the polar modifier methanol, little or no particle formation was expected to occur in the mixing vessel.

The supercritical solution thus formed was introduced into the particle formation vessel 32 (a 50 ml Keystone vessel) via the inner passage of another two-passage coaxial nozzle of the same dimensions as that used in the mixing vessel, together with supercritical nitrogen flowing at 10 l/min (measured at atmospheric conditions) through the outer passage. The particle formation vessel was also maintained at 200 bar and 50°C.

Figure 11:
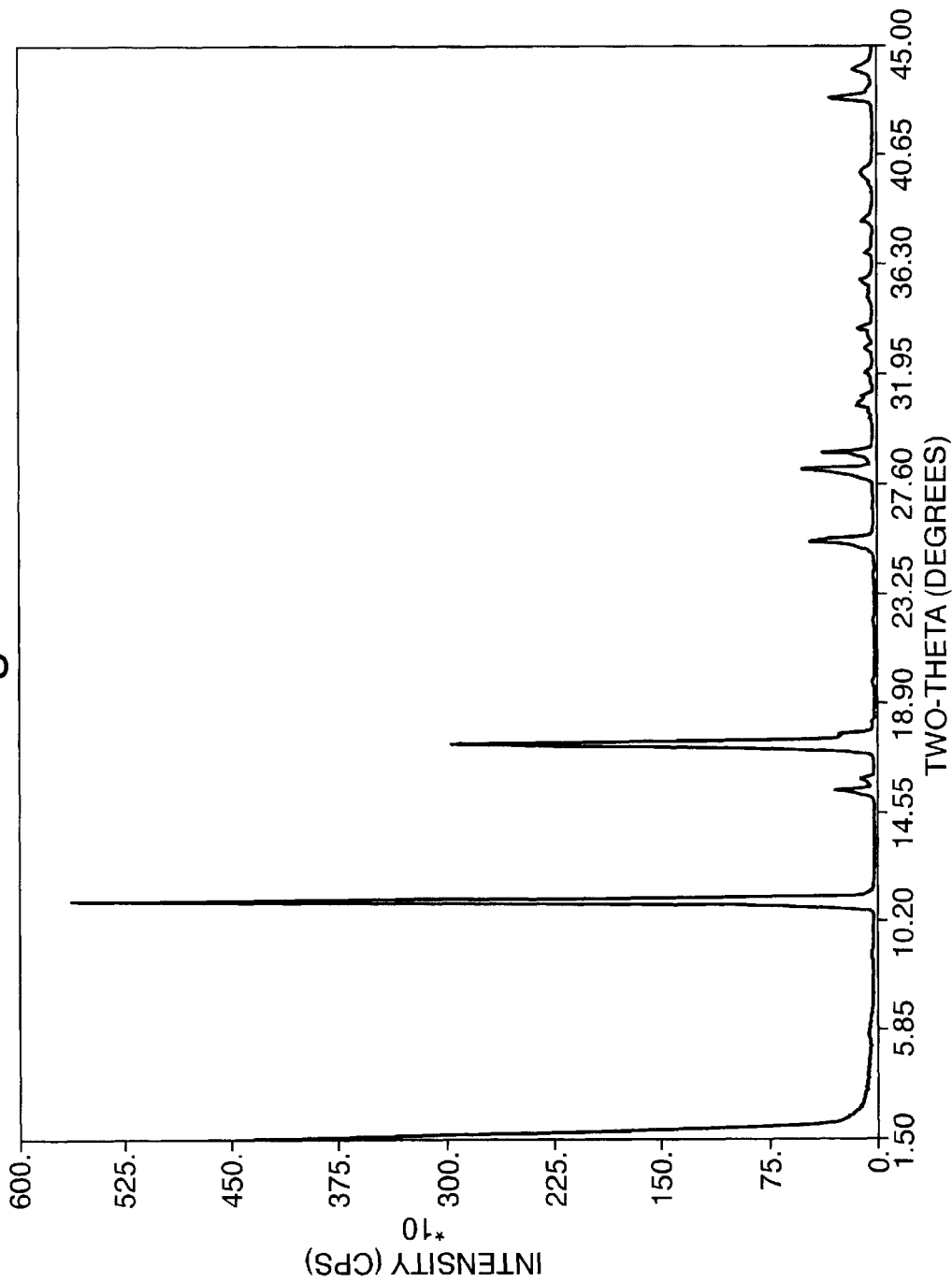

At the end of the run a crystalline white powder was collected in the vessel 32. Its XRPD pattern is shown in FIG. 11.

Example 3b

Example 3a was repeated but starting with a 2% w/v solution of salicylic acid in dichloromethane. Again the dichloromethane acts as a polar modifier, increasing the solubility of the acid in the supercritical carbon dioxide. The fluid flow rates were the same as used in Example 3a, but the operating conditions inside the mixing vessel 25 and the particle formation vessel 32 were 200 bar and 65° C.

Figure 12:
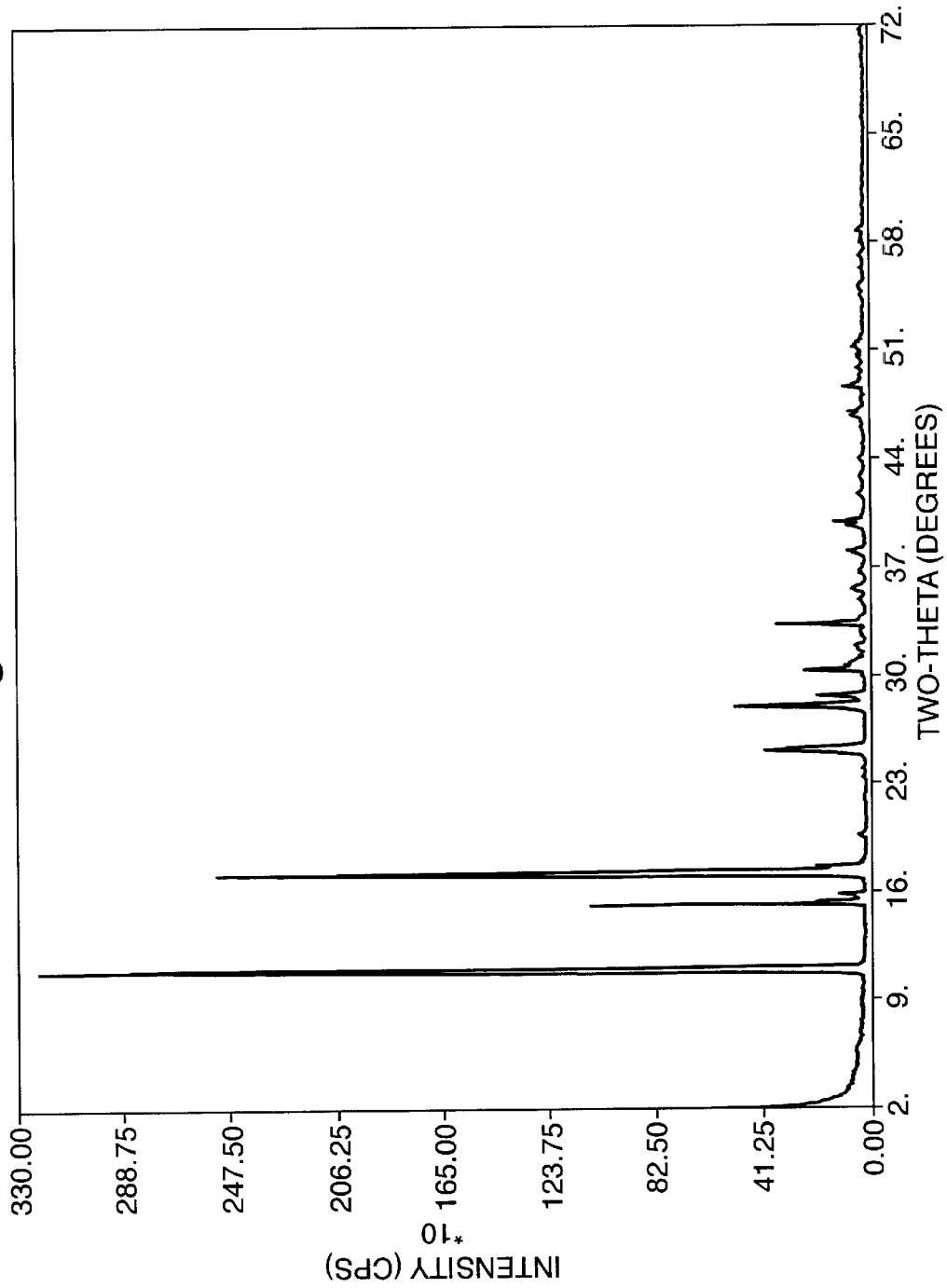

The product was again a fine fluffy white powder, crystalline in form (see FIG. 12).

Example 4

The system described in connection with FIG. 1 was used to produce the drug ketoprofen in particulate form.

0.5 g of ketoprofen was mixed with acid washed glass beads, average diameter 200–300 micron, and packed into a bed inside the sample vessel 5 (in this case, a 5 ml Keystone pressure vessel fitted with 0.5 micron sinters). Supercritical carbon dioxide was then introduced through a frit/sinter at the bottom of the vessel, at a flow rate of 9 ml/min measured at the pump head. The vessel was maintained at 200 bar and 50° C. The sizes of the glass beads were selected to enhance the drug surface area available for contact with the carbon dioxide and also to discourage caking of the bed.

The supercritical solution (of ketoprofen in carbon dioxide) emerging from the top of the sample vessel was introduced into the particle formation vessel 8 (50 ml Keystone) through the inner passage of a two-passage coaxial nozzle of the type used in Example 3, still at a flow rate of 9 ml/min. Supercritical nitrogen was introduced through the outer passage at a flow rate of 10 standard litres/min. The pressure and temperature inside the particle formation vessel were maintained at 200 bar and 50° C.

Figure 13:
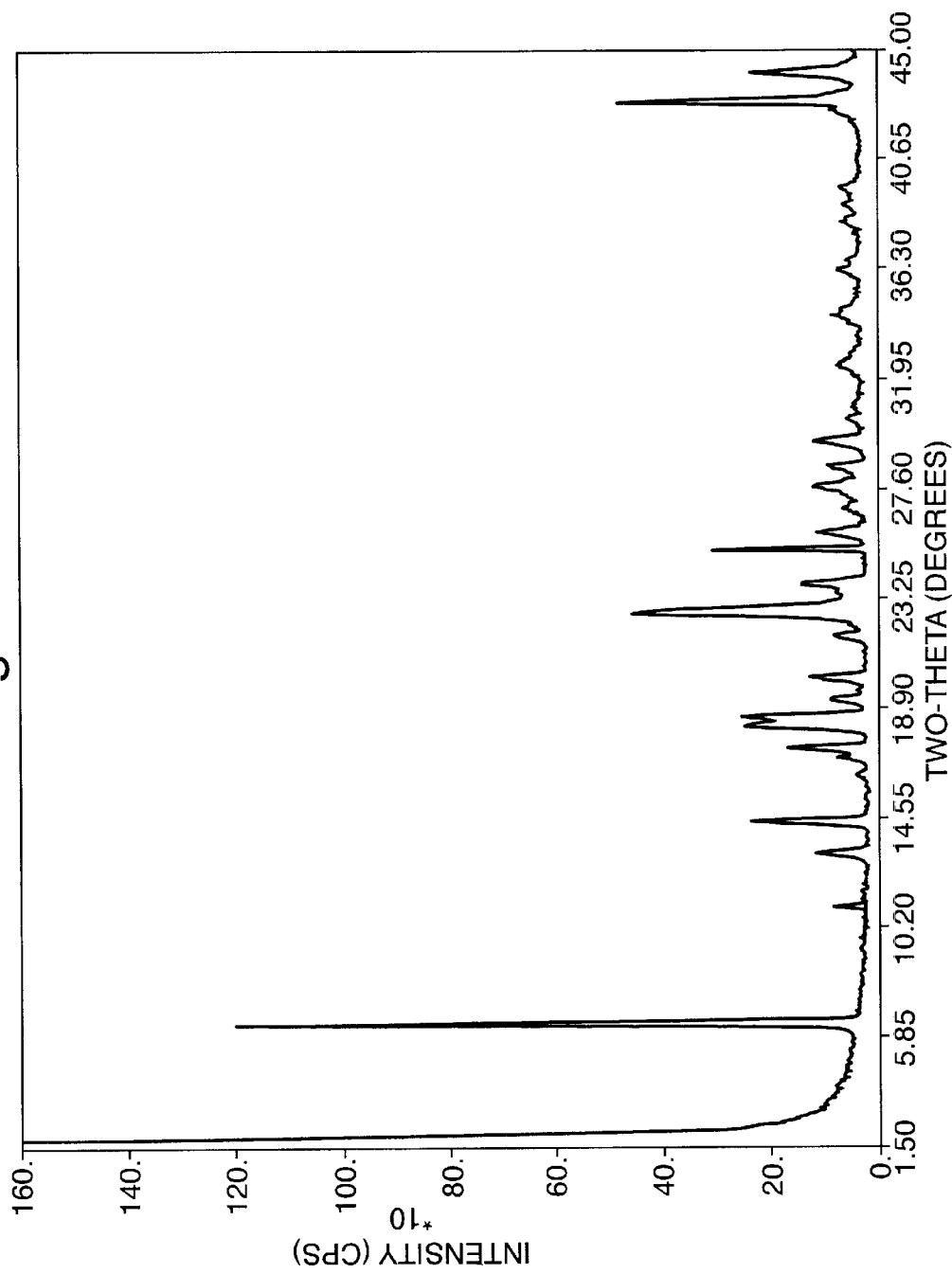

A fine fluffy white powder was collected in the particle formation vessel. Its XRPD pattern (FIG. 13) confirmed its crystallinity.

Example 5

This experiment demonstrates the successful use of the present invention at relatively high operating pressures and temperatures. Experiments were carried out under three different sets of operating conditions (Examples 5a–5c).

For some target substances, high temperatures and pressures are needed in order to produce particles having the desired physicochemical properties. By way of example, to produce the drug salmeterol xinafoate in the form of its polymorph II, pressures greater than 250 bar and temperatures greater than 85° C. are needed. However, applying such "harsh" working conditions is not appropriate for all target substance/fluid combinations. For instance, nicotinic acid has a relatively low solubility in pure and modified supercritical carbon dioxide at pressures below 120 bar and temperatures below 90° C.; under such conditions supercritical carbon dioxide could be used as an anti-solvent to precipitate the acid from solution. However, above 150 bar the solubility of nicotinic acid in supercritical carbon dioxide increases dramatically, and an alternative anti-solvent must be found.

In such a case, the method of the present invention may be used to produce particles of the target substance under the desired high temperature and pressure conditions, despite its solubility, under those conditions, in the first choice of supercritical anti-solvent.

Example 5a

A 0.8% w/v solution of nicotinic acid in methanol was introduced at a rate of 0.2 ml/min, through the inner passage of a nozzle of the type used in Example 3, into the mixing vessel 25 of the FIG. 2 system. The vessel (5 ml Keystone) was maintained at 200 bar and 65° C. Supercritical carbon dioxide was introduced through the outer nozzle passage at a flow rate of 9 ml/min measured at the pump head. The resultant supercritical solution was introduced into a 50 ml Keystone vessel (the particle formation vessel 32) also kept at 200 bar and 65° C., together with supercritical nitrogen flowing at 10 standard litres/min—the same type of nozzle was used, the nicotinic acid solution flowing through the inner passage and the nitrogen through the outer.

Figure 14:
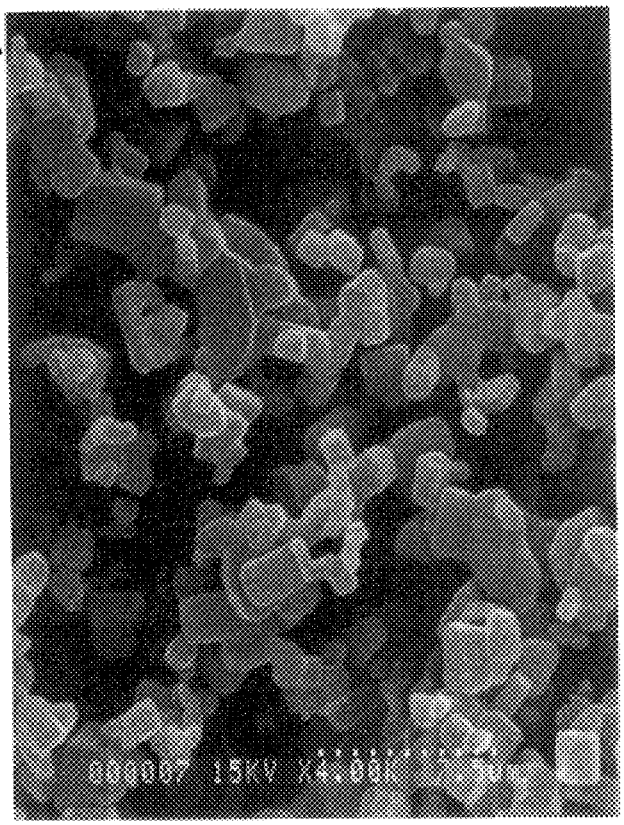
FIGS. 14–18 are SEM (scanning electron microscope) photographs of nicotinic acid produced, respectively, in Example 5a, using SEDS, by a conventional crystallisation and micronisation process and in Examples 5b and 5c.
Figure 15:
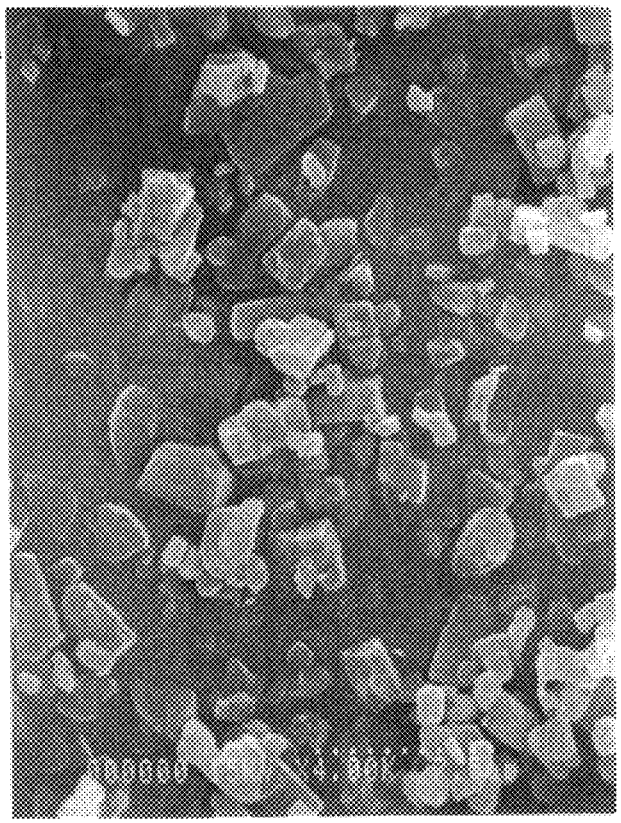
Figure 16:
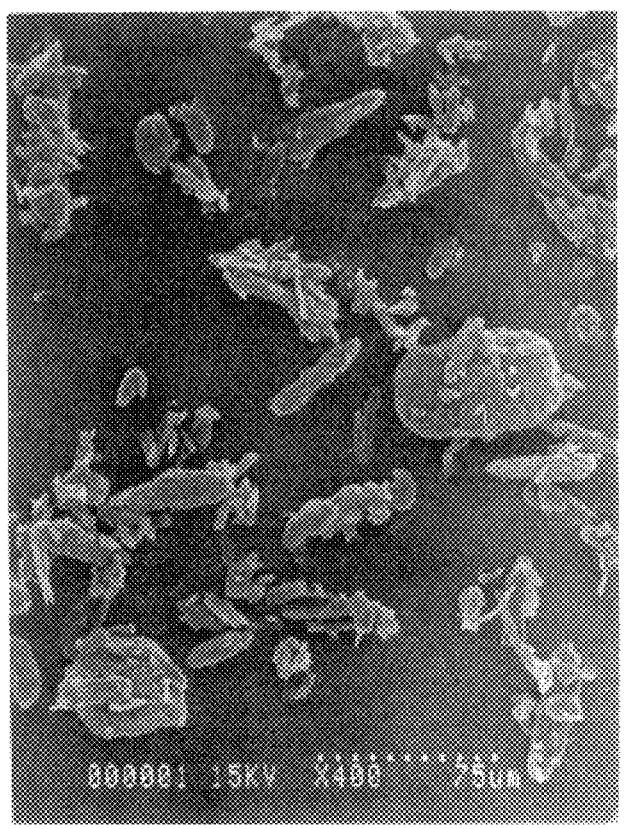

At the end of the run, a fine fluffy white powder was collected in the vessel 32. An SEM micrograph of the product (FIG. 14) shows it to have a similar particle size and morphology to that of nicotinic acid prepared using a SEDS process as described in WO-95/01221 (FIG. 15), but very different to that of the conventionally crystallised and micronised material (FIG. 16). (For the SEDS "control", a 0.8% w/v solution of the acid in absolute ethanol was co-introduced into a particle formation vessel kept at only 90 bar and 85° C., via a two-passage coaxial nozzle, with supercritical carbon dioxide as the anti-solvent; the fluid flow rates were 0.2 ml/min for the acid solution and 9 ml/min (measured at the pump head) for the anti-solvent. It is of note that the same process carried out at 200 bar and 85° C. yielded no product at all, all the nicotinic acid being extracted by the supercritical carbon dioxide and precipitated at the vent line downstream of the particle formation vessel.)

Example 5b

Figure 17:
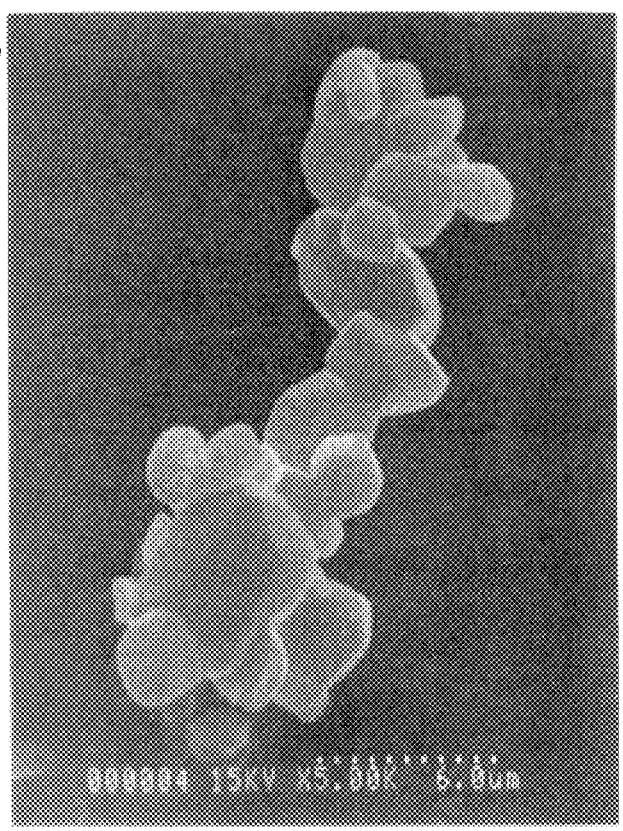

Example 5a was repeated, but at a higher operating temperature of 85° C. The product was again a fine, fluffy white powder, containing well-faceted microcrystals (as seen in FIG. 17) and having a comparable particle size and morphology to that of the product of Example 5a.

Example 5c

Figure 18:
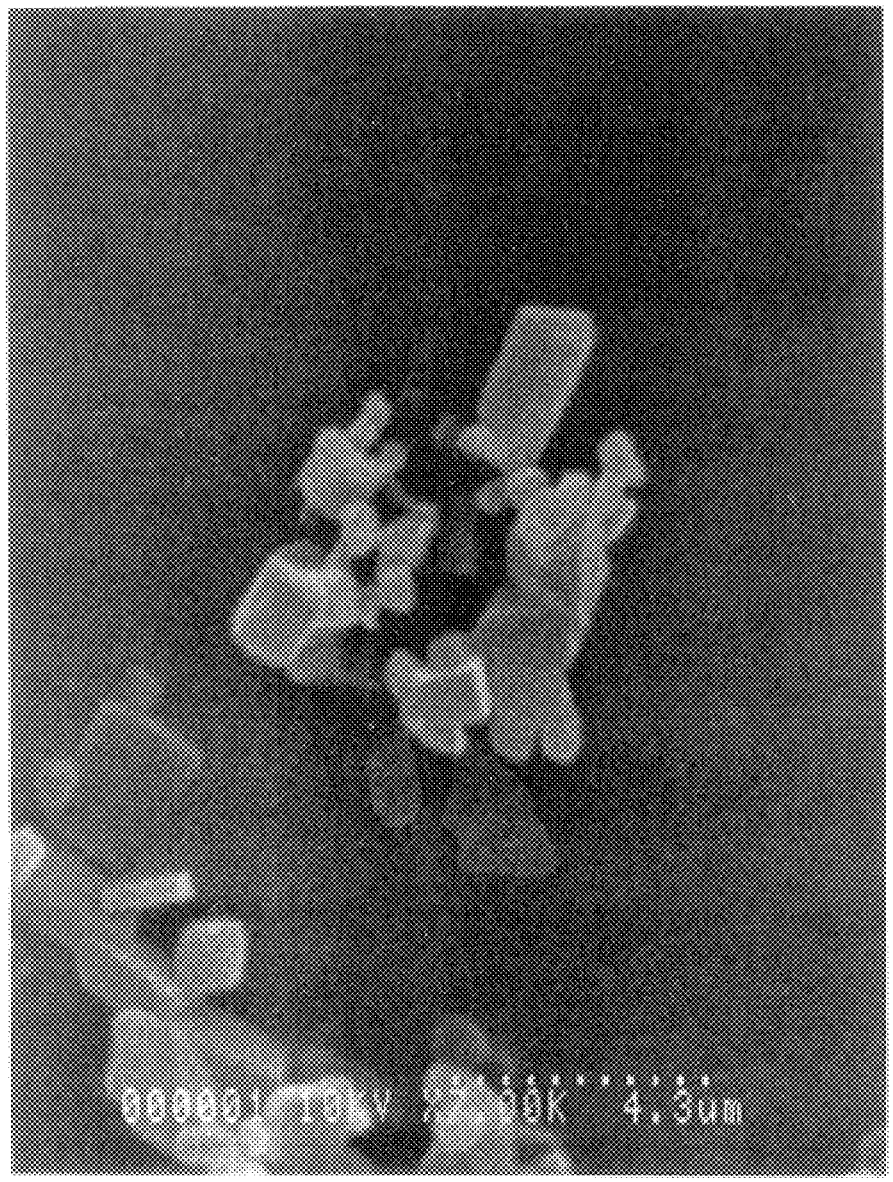

Example 5a was repeated using an operating temperature of 100° C. The product was again a fine fluffy white powder. SEM examination (FIG. 18) revealed a similar morphology to that of the Example 5a product, but surprisingly a smaller particle size. This could be because at higher temperatures the viscosity of the supercritical nicotinic acid/carbon dioxide solution is lowered and its linear velocity at the nozzle outlet therefore raised, thus improving its dispersion by the supercritical nitrogen.

Figure 19:
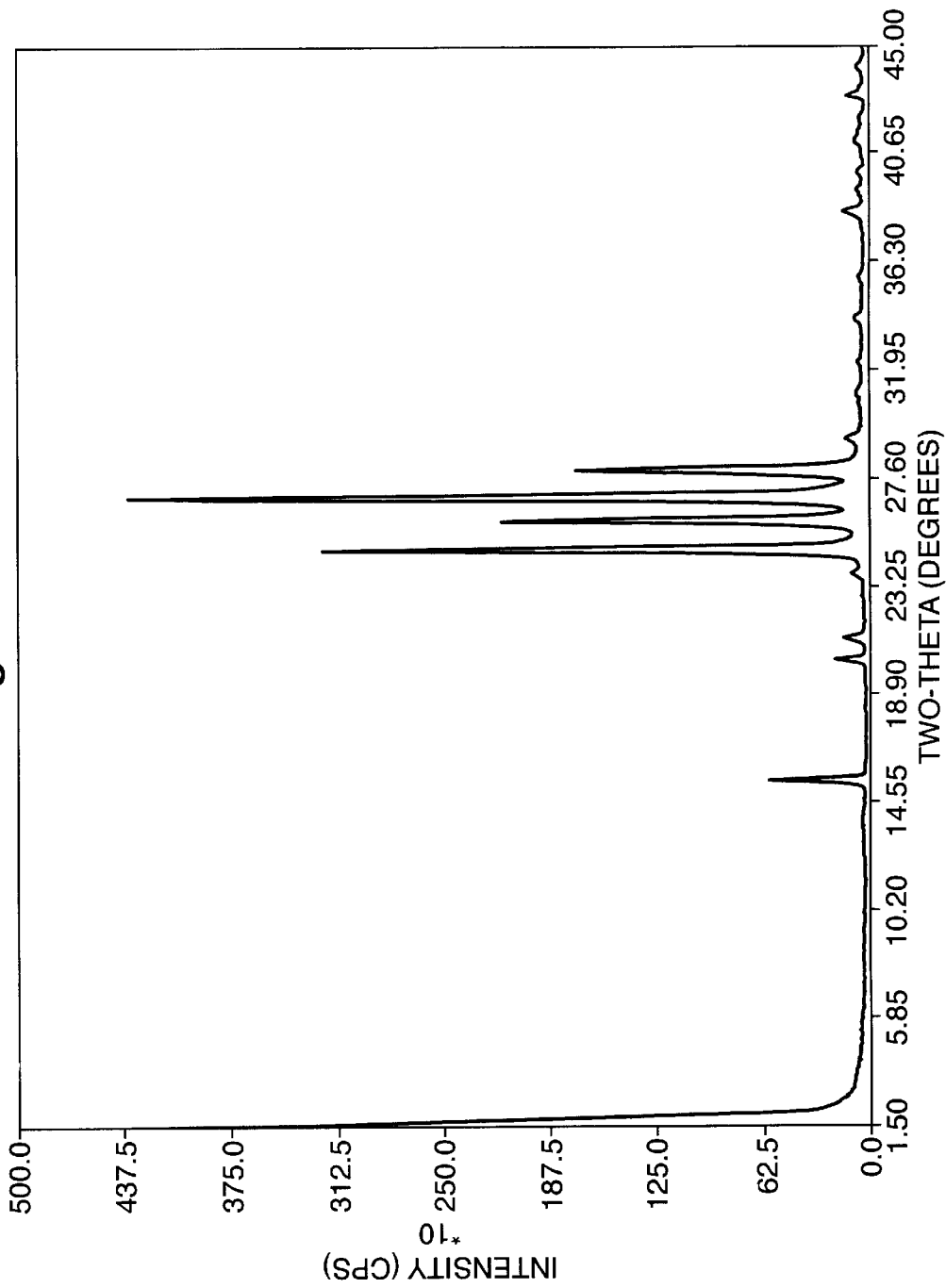
FIGS. 19–21 are XRPD patterns for, respectively, nicotinic acid produced by crystallisation and micronisation and the products of Examples 5a and 5b.
Figure 20:
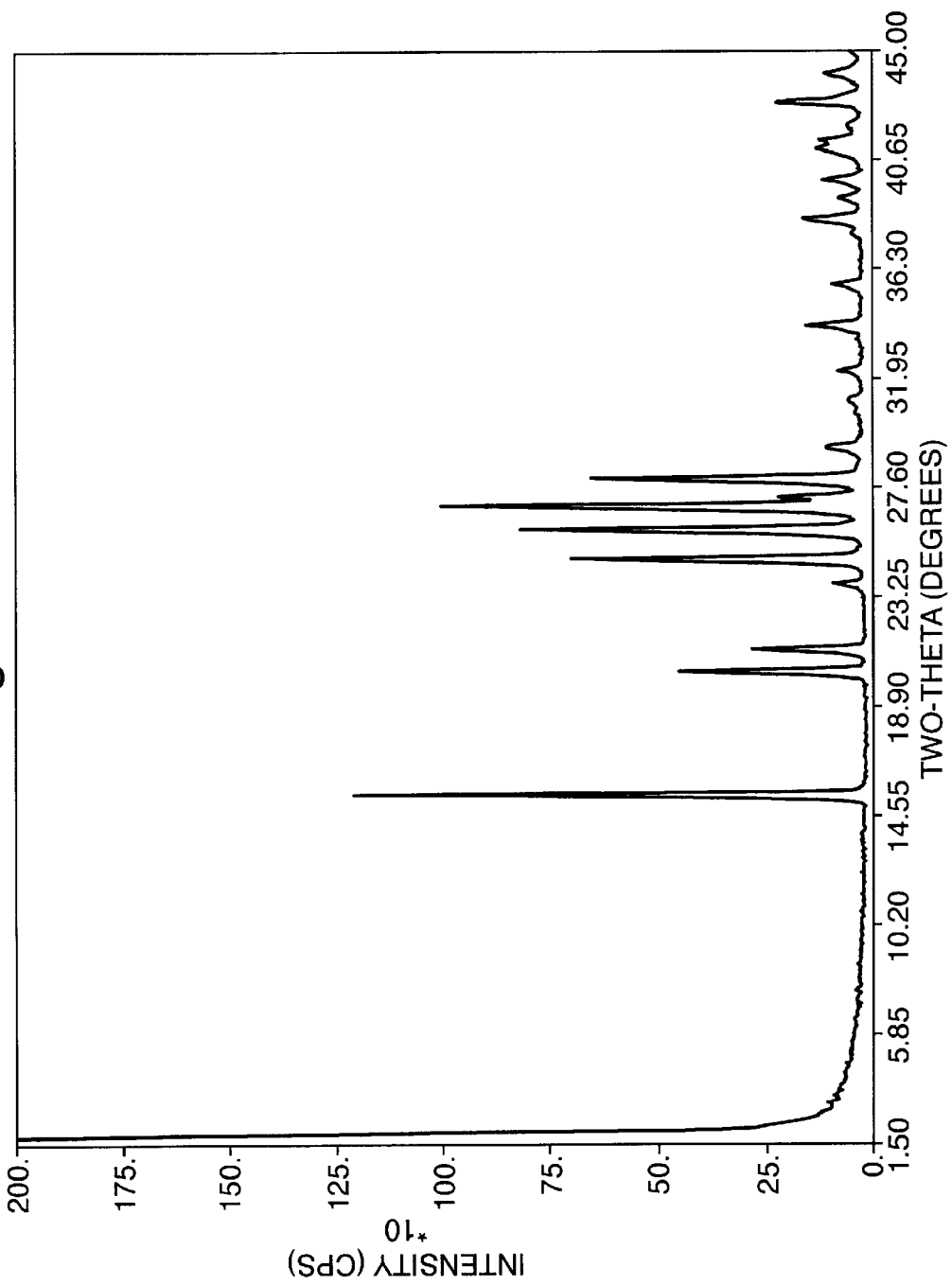
Figure 21:
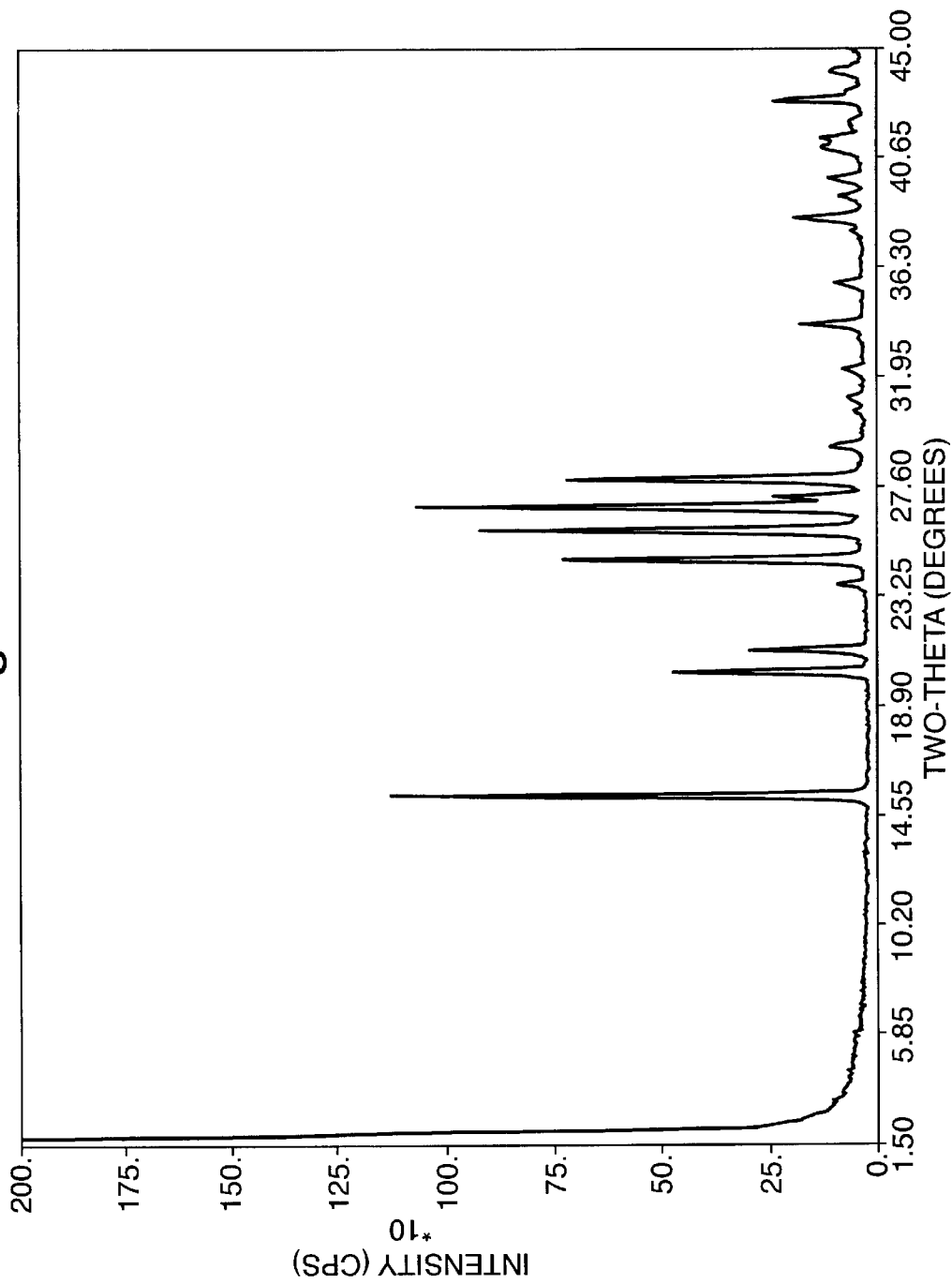

The product of Examples 5a–5c exhibited a high degree of crystallinity, and the same morphology as a micronised form of nicotinic acid—see the XRPD patterns of FIG. 19 (the micronised product), 20 (the product of Example 5a) and 21 (that of Example 5b).

What is claimed is:

1. A method for forming particles of a target substance, the method comprising:
    (a) preparing a target solution, containing the target substance dissolved in a vehicle which is either a near-critical fluid or a first supercritical fluid;
    (b) introducing the target solution into a particle formation vessel; and
    (c) contacting the target solution, in the particle formation vessel, with a second supercritical fluid, under conditions which allow the second supercritical fluid to cause precipitation of particles of the target substance from the target solution;
       wherein the second supercritical fluid is miscible or substantially miscible with the vehicle and is a fluid in which the target substance is insoluble or substantially insoluble.

2. A method according to claim 1, wherein the second supercritical fluid and the target solution are co-introduced into the particle formation vessel with coaxial or substantially coaxial flows, using as the fluid inlet a nozzle having an outlet end communicating with the interior of the particle formation vessel and two or more coaxial passages which terminate adjacent or substantially adjacent one another at the outlet end, at least one of the passages serving to introduce a flow of the second supercritical fluid, and at least one of the passages serving to introduce a flow of the target solution.

3. A method according to claim 2, wherein the vehicle is supercritical carbon dioxide.

4. A method according to claim 1, wherein the vehicle contains one or more modifiers.

5. A method according to claim 1, wherein the second supercritical fluid is supercritical nitrogen.

6. A method according to claim 1 or claim 4 wherein the second supercritical fluid is supercritical nitrogen.

7. A method according to claim 1, wherein the second supercritical fluid contains one or more modifiers.

8. A method according to claim 1, wherein the flow rate of the second supercritical fluid into the particle formation vessel, measured at or immediately prior to its contact with the target solution, is higher than that of the target solution.

9. A method according to claim 8, wherein the flow rates of the second supercritical fluid and the target solution are such that the vehicle constitutes between 1 and 20 mole % of the fluid mixture formed when the fluids come into contact with one another.

10. A method according to claim 1, involving producing a solution of the target substance in a primary solvent in which it is more soluble than in the vehicle; dissolving the resultant solution in the vehicle or a sub-critical form thereof; and then contacting the resulting solution, in the form of a supercritical or near-critical fluid, with the second supercritical fluid in the particle formation vessel.

11. A method according to claim 10, wherein the solution of the target substance in the primary solvent is dissolved in the vehicle by dispersing the solution into a fluid mixing vessel together with the vehicle, using a fluid inlet which allows both the solution and the vehicle to enter the vessel at the same or substantially the same point, which is also the same as, or substantially the same as, the point where they meet, and which allows the vehicle to disperse the solution at or substantially at the point where the fluids enter the fluid mixing vessel.

12. Apparatus for use in carrying out a method according to claim 10, the apparatus comprising a particle formation vessel; a controller for controlling the temperature and pressure in the particle formation vessel at desired levels; a fluid mixing vessel; a controller for controlling the temperature and pressure in the fluid mixing vessel at desired levels; first fluid inlet a controller for introducing into the fluid mixing vessel a vehicle and a primary solution of a target substance in a primary solvent, so as to form in the fluid mixing vessel a target solution of the target substance and the primary solvent in the vehicle; and a second fluid inlet for introducing the target solution thus formed, preferably together with a second supercritical fluid, into the particle formation vessel;
   wherein the first fluid inlet allows both the primary solution and the vehicle to enter the fluid mixing vessel at the same or substantially the same point, which is also the same as, or substantially the same as, the point where they meet, and wherein the first fluid inlet also allows the vehicle to disperse the primary solution at or substantially at the point where the fluids enter the fluid mixing vessel.

13. A method according to claim 1, wherein the target solution and the second supercritical fluid are co-introduced into the particle formation vessel through a fluid inlet which allows them both to enter the vessel at the same or substantially the same point, which is also the same as, or substantially the same as, the point where they meet, at which point the second supercritical fluid is able to disperse the target solution and simultaneously to cause particle precipitation from it.

14. A method according to claim 8, wherein the target substance is dissolved directly in the vehicle and the resultant solution is introduced into the particle formation vessel to contact the second supercritical fluid.

15. Apparatus according to claim 12, wherein the second fluid inlet allows both the target solution and the second supercritical fluid to enter the particle formation vessel at the same or substantially the same point, which is also the same as, or substantially the same as, the point where they meet, and which allows the second supercritical fluid to disperse the target solution at or substantially at the point where the fluids enter the vessel.

* * * * *